United States Patent
Huang et al.

(10) Patent No.: US 12,382,919 B2
(45) Date of Patent: Aug. 12, 2025

(54) MATERIALS AND METHODS FOR PRODUCING HYBRID DIPLOID POTATO

(71) Applicant: AGRICULTURAL GENOMICS INSTITUTE AT SHENZHEN, CHINESE ACADEMY OF AGRICULTURAL SCIENCES, Shenzhen (CN)

(72) Inventors: Sanwen Huang, Shenzhen (CN); Chunzhi Zhang, Shenzhen (CN); Yanhui Zhu, Shenzhen (CN); Pei Wang, Shenzhen (CN); Zhongmin Yang, Shenzhen (CN); Die Tang, Shenzhen (CN)

(73) Assignee: AGRICULTURAL GENOMICS INSTITUTE AT SHENZHEN, CHINESE ACADEMY OF AGRICULTURAL SCIENCES, Shenzhen (CN)

( * ) Notice: Subject to any disclaimer, the term of this patent is extended or adjusted under 35 U.S.C. 154(b) by 265 days.

(21) Appl. No.: 17/976,237

(22) Filed: Oct. 28, 2022

(65) Prior Publication Data

US 2023/0165212 A1    Jun. 1, 2023

Related U.S. Application Data

(60) Provisional application No. 63/341,216, filed on May 12, 2022, provisional application No. 63/273,470, filed on Oct. 29, 2021.

(51) Int. Cl.
    A01H 5/06    (2018.01)
    A01H 6/82    (2018.01)

(52) U.S. Cl.
    CPC .............. *A01H 6/827* (2018.05); *A01H 5/06* (2013.01)

(58) Field of Classification Search
    None
    See application file for complete search history.

(56) References Cited

U.S. PATENT DOCUMENTS 11,140,841 B2    10/2021    Lindhout et al.

OTHER PUBLICATIONS

Dzidzienyo et al. Theor Appl Genet (2016)129:1985-2001.*
Bethke, P.C., et al., "History and origin of Russet Burbank (Netted Gem) a sport of Burbank." *Am. J. Potato Res.* 91, 594-609 (2014).
Bonierbale, M.W., et al. "RFLP maps based on a common sets of clones reveal modes of chromosomal evolution in potato and tomato." *Genetics* 120, 1095-1103 (1988).
Bruna, T., et al. "GeneMark-EP+: eukaryotic gene prediction with self-training in the space of genes and proteins." *NAR Genom. Bioinform.* 2, 1qaa026 (2020).
Chaisson, M.J., et al. "Mapping single molecule sequencing reads using basic local alignment with successive refinement (BLASR): application and theory." *BMC Bioinformatics* 13, 238 (2012).
Charlesworth, D., et al. "The genetics of inbreeding depression." *Nat. Rev. Genet.* 10, 783-796 (2009).
Clot, C.R., et al. "The origin and widespread occurrence of Sli-based self-compatibility in potato." *Theor. Appl. Genet.* 133, 2713-2728 (2020).
Cui, J., et al. "Feedback regulation of DYT1 by interactions with downstream bHLH factors promotes DYT1 nuclear localization and anther development." *Plant Cell* 28, 1078-1093 (2016).
Dudchenko, O., et al. "De novo assembly of the Aedes aegypti genome using Hi—C yields chromosome-length scaffolds." *Science* 356, 92-95 (2017).
Duncan, et al. "The production of callus capable of plant regeneration from immature embyros of numerous *Zea mays* genotypes." *Planta,* 165, 322-332 (1985).
Durand, N.C., et al. "Jucier provides a one-click system for analyzing Loop-resolution Hi—C experiments." *Cell Syst.* 3, 95-98 (2016).
Emms, D.M., et al. "OrthoFinder: solving fundamental biases in whole genome comparisons dramatically improves orthogroup inference accuracy." *Genome Biol.* 16, 157 (2015).
Enciso-Rodriquez, F., et al. "Overcoming self-incompatibility in diploid potato using CRISPR-Cas9. Front." *Plant Sci.* 10, 376 (2019).
Grabherr, M.G., et al. "Full-length transcriptome assembly from RNA-Seq data without a reference genome." *Nat. Biotechnol.* 29, 644-652 (2011).
Haas, B.J., et al. "Improving the *Arabidopsis* genome annotation using maximal transcript alignment assemblies." *Nucleic Acids Res.* 31, 5654-5666 (2003).
Haas, B.J., et al. "Automated eukaryotic gene structure annotation using EVidenceModeler and the Program to Assemble Spliced Alignments." *Genome Biol.* 9, R7 (2008).
Hardigan, M.A., et al. "Genome diversity of tuber-bearing Solanum uncovers complex evolutionary history and targets of domestication in the cultivated potato." *Proc. Natl. Acad. Sci. USA* 114, E9999-E10008 (2017).

(Continued)

*Primary Examiner* — Medina A Ibrahim
(74) *Attorney, Agent, or Firm* — Arnold & Porter Kaye Scholer LLP

(57) ABSTRACT

Provided herein are materials and methods for producing diploid, fertile, uniform, and vigorous hybrid potato. Also provided are methods of using advanced breeding methods, such as genome design, to generate potato inbred lines with high homozygosity which enables the exploitation of heterosis in this tuber crop and transforms potato breeding from a slow, non-accumulative mode into a fast-iterative one.

11 Claims, 6 Drawing Sheets

(56) References Cited

OTHER PUBLICATIONS

Hosaka, K., et al. "Genetics of self-compatibility in a self-incompatible wild diploid potato species *Solanum chacoense*. 2. Localization of an S-locus inhibitor (Sli) gene on the potato genome using DNA markers." *Euphytica* 103, 265-271 (1998).
Huang, W., et al. "Induced High-Yield Production of zeaxanthin, lutein, and beta-carotene by a mutant of chlorella zofingiensis." *J. Agric. Food. Chem.* 66, 891-897 (2018).
Jansky, S.H., et al. "Reinventing potato as a diploid inbred line-based crop." *Crop Sci.* 56, 1412-1422 (2016).
Kamo et al., "Regeneration of *Zea mays* L. From Embryogenic Callus", *Bot. Gaz.*, 146, 327-334 (1985).
Kloosterman, B., et al. "From QTL to candidate gene: Genetical genomics of simple and complex traits in potato using a pooling strategy." *BMC Genomics* 11, 158 (2010).
Kolmogorov, M., et al. "Assembly of long, error-prone reads using repeat graphs." *Nat. Biotechnol.* 37, 540-546 (2019).
Korf, I. "Gene finding in novel genomes."*BMC bioinformatics* 5, 59 (2004).
Kronenberg, Z.N., et al. "High-resolution comparative analysis of great ape genomes." *Science* 360, eaar6343 (2018).
Li, H. "Aligning sequence reads, clone sequences and assembly contigs with BWA-MEM." *arXiv*, 1303.3997 (2013).
Li, H., et al. "The Sequence Alignment/Map (SAM) Format and SAMtools." *Bioinformatics* 25, 1653-1654 (2009).
Li, Y., et al. "Prospects of diploid hybrid breeding in potato." *Chinese Potato* 27, 96-99 (2013).
Lindhout, P., et al. "Towards F1 hybrid seed potato breeding." *Potato Res.* 54, 301-312 (2011).
Manary, M., et al. "Identification of pathogen genomic variants through an integrated pipeline." *BMC Bioinformatics* 15, 63 (2014).
Manrique-Carpintero, et al. "Comparative analysis of regions with distorted segregation in three diploid populations of potato." *G3: Genes, Genomes, Genetics* 6:8: 2617-2628 (2016).
Miki, et al. "In: Methods in Plant Molecular Biology and Biotechnology," Glick and Thompson (Eds.), CRC Press, Inc. Boca Raton, 1993.
Pertea, M., et al. "Transcript-level expression analysis of RNA-seq experiments with HISAT, StringTie and Ballgown." *Nat. Protoc.* 11, 1650-1667 (2016).
Pertea, M., et al. "StringTie enables improved reconstruction of a transcriptome from RNA-seq reads." *Nat. Biotechnol.* 33, 290-295 (2015).
Peterson, B.A., et al. "Self-fertility in a cultivated diploid potato population examined with the Infinium 8303 potato single-nucleotide polymorphism array." *Plant Genome* 9, 1-13 (2016).
PGSC. "Genome sequence and analysis of the tuber crop potato." *Nature* 475, 189-195 (2011).
Sharma, S.K., et al. "Construction of reference chromosome-scale pseudomolecules for potato: integrating the potato genome with genetic and physical maps." *G3: Genes, Genomes, Genetics* 3, 2031-2047 (2013).
Spooner, D.M., et al. "Systematics, diversity, genetics, and evolution of wild and cultivated potatoes." *Bot. Rev.* 80, 283-383 (2014).
Stanke, M., et al. "AUGUSTUS: a web server for gene finding in eukaryotes." *Nucleic Acids Res.* 32, W309-312 (2004).
Stokstad, E., "The new potato." *Science* 363, 574-577 (2019).
Takagi, H., et al. "QTL-seq: rapid mapping of quantitative trait loci in rice by whole genome resequencing of DNA from two bulked populations." *Plant J.* 74, 174-183 (2013).
Takayama, S., et al. "Self-incompatibility in plants. Annu. Rev." *Plant Biol.* 56, 467-489 (2005).
Van Eck, H.J., et al. "Multiple alleles for tuber shape in diploid potato detected by qualitative and quantitative genetic analysis using RFLPs." *Genetics* 137, 303-309 (1994).
Van Lieshout, N., et al. Solyntus, the new highly contiguous reference genome for potato (*Solanum tuberosum*).: *G3: Genes, Genomes, Genetics* 10, 3489-3495 (2020).
Vaser, R., et al. "SIFT missense predictions for genomes." *Nat. Protoc.* 11, 1-9 (2016).
West et al. "Embryogenesis in Higher Plants: An Overview", *The Plant Cell*, 5, 1361-1369 (1993).
Xing, H., et al. "A CRISPR/Cas9 toolkit for multiplex genome editing in plants." *BMC Plant Biol.* 14, 327 (2014).
Ye, M., et al. "Generation of self-compatible diploid potato by knockout of S-RNase." *Nat. Plants* 4, 651-654 (2018).
Zhang, C., et al. "The genetic basis of inbreeding depression in potato." *Nat. Genet.* 51, 374-378 (2019).
Zhang, C., et al. "Genome design of hybrid potato." *Cell*, 184(15), 3873-3883 (2021).

* cited by examiner

MATERIALS AND METHODS FOR PRODUCING HYBRID DIPLOID POTATO

CROSS-REFERENCE TO RELATED APPLICATIONS

This application claims the benefit of U.S. Provisional Application No. 63/273,470, filed Oct. 29, 2021, and U.S. Provisional Application No. 63/341,216, filed May 12, 2022, both of which are incorporated by reference herein in their entireties.

FIELD

The present disclosure relates generally to the field of plant breeding and genetics, and more specifically to materials and methods for producing hybrid diploid potato.

BACKGROUND

As the most important tuber crop, potato (*Solanum tuberosum* L.) is a staple food for some 1.3 billion people worldwide. However, compared with other major crops, the genetic gains in potato have been small. The complexity of tetrasomic inheritance is a key factor hampering the genetic improvement of cultivated potato. For example, the 118-year-old 'Russet Burbank' is still the foremost processing cultivar, despite it being susceptible to many major diseases (Bethke et al., 2014). Clonal propagation is another constraint for the potato industry, involving ~10% of the total production costs and bears a very significant carbon footprint for tuber production associated with pest control, storage, and shipment to farmers.

To address these problems, efforts were attempted to convert potato into an inbred-line-based diploid crop, propagated by seeds (Jansky et al., 2016; Li et al., 2013; Lindhout et al., 2011). Indeed, ~70% of the natural potato germplasm, including wild species and landraces, are diploid (Spooner et al., 2014), the extensive diversity of which has yet to be exploited. Sophisticated genetic populations, such as recombinant inbred lines (RILs), introgression lines (ILs), multiparent advanced generation intercrosses populations (MAGICs), and nested association mapping populations (NAMs), can be developed using inbred lines of various lineages to facilitate trait gene discovery. Breeding with inbred lines is a fast and iterative process, using backcrossing to incorporate one or few beneficial alleles once in a generation, a process not amenable with the conventional auto-tetraploid potato breeding, which is essentially non-accumulative. Therefore, converting conventional potato into a seed crop, hybrid potato, would lead to a "Green Revolution" in the potato industry, with immense benefits for consumers.

However, effective hybrid potato breeding relies on the establishment of pure inbred parental lines, and the production of diploid homozygotes in potato is hampered by two phenomena: i) self-incompatibility, i.e., a genetic system that prevents self-fertilization through rejection of self-pollen, and ii) inbreeding depression, i.e., the gradual reduction in fertility and vigor upon continued self-fertilization.

Accordingly, there is a need for improved materials and methods. Particularly, there is a need for using advanced genetics and breeding methods, such as genome design, for developing inbred potato lines with high homozygosity in order to produce hybrid potato varieties with strong vigor and high uniformity.

BRIEF SUMMARY

Provided herein are plant materials for producing diploid, fertile, uniform, and vigorous $F_1$ hybrid potato varieties. Also provided are methods of using advanced breeding methods, such as genome design, to generate potato inbred lines with high homozygosity, which enables the exploitation of heterosis in this tuber crop and transforms potato breeding from a slow, non-accumulative mode into a fast-iterative one.

In one aspect, provided herein is a diploid, fertile, self-compatible inbred potato line selected from the group consisting of "A6-10", "E4-63", and "E4-64", representative seeds of which having been deposited at the China Center for Type Culture Collection (CCTCC) under accession numbers P202204, P202212, and P202220, respectively.

In another aspect, provided herein is an inbred diploid potato line, wherein the inbred diploid potato line is fertile, self-compatible, and has at least 90% of genome homozygosity.

In yet another aspect, provided herein is a self-compatible and fertile inbred diploid potato line, having at least 90% of genome homozygosity.

In still another aspect, provided herein is a diploid, fertile, and self-compatible potato line, wherein at least 85% of its genomic loci are in homozygous state, wherein the self-compatibility in the potato line is conferred by: 1) a low-expressed S-RNase allele $S_{S11}$ as found in potato clone "A6-10", representative seeds of which having been deposited with CCTCC under accession number P202204, or 2) a S-locus inhibitor (Sli) gene as found in potato clone "E4-63" or "E4-64", representative seeds of which having been deposited with CCTCC under accession number P202212 and P202220, respectively.

In some embodiments, the inbred diploid potato line disclosed herein comprises one or more beneficial alleles selected from the group consisting of an S-RNase S11 ($S_{S11}$) allele for self-compatibility, a Yellow Leaf 1 (YL1) allele for normal leaves, a Floral Bud Abortion 1 (FBA1) allele for fertility, and a Yellow (Y) allele for yellow tuber flesh.

In still another aspect, provided herein is an inbred diploid potato line, comprising a beneficial Yellow Leaf 1 (YL1) allele and a beneficial Large-Effect Deleterious Mutation 1 (LED1) allele in the coupling phase.

In still another aspect, provided herein is an essentially derived variety (EDV) of the inbred potato line disclosed herein.

In still another aspect, provided herein is an $F_1$ progeny of the inbred potato line disclosed herein.

In still another aspect, provided herein is an $F_1$ hybrid diploid potato line having two parental inbred potato lines, wherein each of the two parental inbred lines has a genome homozygosity of at least 90%, wherein the genome homozygosity is determined by the formula: (length of homozygous bins÷potato genome size)×100%.

In still another aspect, provided herein is an $F_1$ hybrid diploid potato line having two parental inbred potato lines, wherein the two parental inbred lines comprise different self-compatibility genes.

In some embodiments of the $F_1$ hybrid potato line disclosed herein, the tuber yield of the $F_1$ hybrid is at least 30% higher than the average tuber yield of the two parental lines grown in the field.

In some embodiments of the $F_1$ hybrid potato line disclosed herein, the hybrid potato line has a tuber yield of at least 250 grams per plant.

In some embodiments, the potato line disclosed herein comprises at least one agronomically desired trait selected from the group consisting of strong growth vigor, high yield, improved nutritional value, insect tolerance, nematode resistance, disease resistance, herbicide tolerance, cold tolerance, drought tolerance, wet tolerance, tolerance to dry and wet rot, salinity tolerance, and cold-sweetening resistance.

In some embodiments of the potato line disclosed herein, the potato line produces tubers having a carotenoid content of at least 40 mg/kg dry-weight and/or a dry matter percentage of at least 20%.

In some aspect, provided herein is a plant of the potato line disclosed herein.

In some aspect, provided herein is a seed or a tuber of the plant disclosed herein.

In some aspect, provided herein is a plant part from the plant disclosed herein.

In some embodiments of the plant part disclosed herein, the plant part is a seed, a tuber, a leaf, a flower, a fruit, a cell, a tissue, an organ, or a portion thereof.

In still another aspect, provided herein is a tissue culture produced from a protoplast or a cell of the plant disclosed herein, wherein the protoplast or cell is derived from a plant part of the plant selected from the group consisting of leaf, pollen, embryo, cotyledon, hypocotyl, meristematic root cell, root tip, pistil, anther, ovule, flower, shoot, stem, seed, and petiole.

In still another aspect, provided herein is a method for producing $F_1$ hybrid potato seed, comprising: obtaining a first self-compatible diploid potato plant and a second self-compatible diploid potato plant; selfing the first self-compatible diploid potato plant to obtain a first progeny population and selfing the second self-compatible diploid potato plant to obtain a second progeny population; selecting from the first and second progeny populations one or more progeny potato plants having genome homozygosity of at least 60%; repeating steps (b) to (c) 2 to 4 times on the selected progeny plant in each of the first and second progeny populations to obtain inbred potato lines having at least 90% of genome homozygosity; and generating $F_1$ hybrid potato seed by crossing an inbred line from the first progeny population and an inbred line from the second progeny population.

In still another aspect, provided herein is a method for producing $F_1$ hybrid potato seed, comprising: obtaining a first self-compatible diploid potato clone and a second self-compatible diploid potato clone; selfing the first self-compatible diploid potato clone to obtain a first progeny population and selfing the second self-compatible diploid potato clone to obtain a second progeny population; performing genetic analysis on the first and second progeny populations to identify deleterious mutations and beneficial alleles in the genomes of the progeny populations; using genome-assisted selection to select progeny lines having fewer deleterious mutations and more beneficial alleles in each of the first and second progeny populations; repeating steps (b) to (d) 2 to 4 times on the selected progeny lines in each of the first and second progeny populations to obtain inbred potato lines having at least 90% of genome homozygosity; and generating $F_1$ hybrid potato seed by crossing an inbred line from the first progeny population and an inbred line from the second progeny population.

In some embodiments, the method disclosed herein further comprises a genetic analysis of genome-wide segregation distortions (SDs) in the progeny populations.

In some embodiments of the method disclosed herein, the genome-assisted selection comprises reducing the number of deleterious mutations, breaking tight linkage of deleterious mutations, and/or stacking beneficial alleles in the genome.

In some embodiments of the method disclosed herein, the deleterious mutations and/or beneficial alleles are associated with gametic or zygotic survival, growth vigor, leaf chlorosis, flower development, fertility, tuber size, tuber number per plant, tuber shape, tuber flesh color, or a combination thereof.

In still another aspect, provided herein is a method for producing a hybrid potato seed, the method comprising crossing a first potato plant with a second potato plant and harvesting a hybrid potato seed resulting from the cross, wherein the first or second parent potato plant is derived from an inbred diploid potato line disclosed herein.

In still another aspect, provided herein is a method for producing a hybrid potato plant, the method comprising producing a seed according to the method disclosed herein, and growing the seed into a potato plant.

In still another aspect, provided herein is a method for producing a hybrid potato line, the method comprising: providing a first potato plant, wherein the first potato plant is a plant of potato line "A6-10", representative seeds of which having been deposited with CCTCC under accession number P202204; providing a second potato plant, wherein the second potato plant is a plant of potato line "E4-63" or "E4-64", representative seeds of which having been deposited with CCTCC under accession number P202212 and P202220, respectively; and cross-pollinating the first potato plant and the second potato plant to provide seeds and collecting the seeds to thereby provide a hybrid potato line.

In still another aspect, provided herein is a method for producing a vigorous $F_1$ hybrid potato line, the method comprising: providing a plurality of inbred potato lines; analyzing the genomes of the plurality of inbred potato lines to identify deleterious alleles and beneficial alleles in the genomes; calculating genome complementarity scores between the plurality of inbred potato lines based on the identified deleterious alleles and beneficial alleles in the genomes; selecting from the plurality of inbred potato lines a subset of inbred potato lines based on the calculated genome complementarity scores; and crossing the selected subset of inbred potato lines to obtain vigorous $F_1$ hybrid lines.

Fine mapping of the FBA1 gene by recombinant screening. N, number of recombinant plants with the same phenotype. Dark grey bars indicate the homozygous recessive genotype of fba1, and light grey bars indicate heterozygous genotype. 1719, 1711 and 1712 represent PGSC0003DMG400021719, PGSC0003DMG400021711 and PGSC0003DMG400021712, respectively. (D) Relative expression of the FBA1 candidate in the floral buds of normal and bud-abortion plants. Values are mean+SD, n=3 biological replicates. Asterisks represent significant differences between FBA1 and mutant determined by Student's t test. **p<0.01. (E) Knockout of the PGSC0003DMG400021719 in potato by genome editing. (F) Phenotype of genome-edited fba1 mutants. Scale bar represents 0.5 cm.

Figure 4:
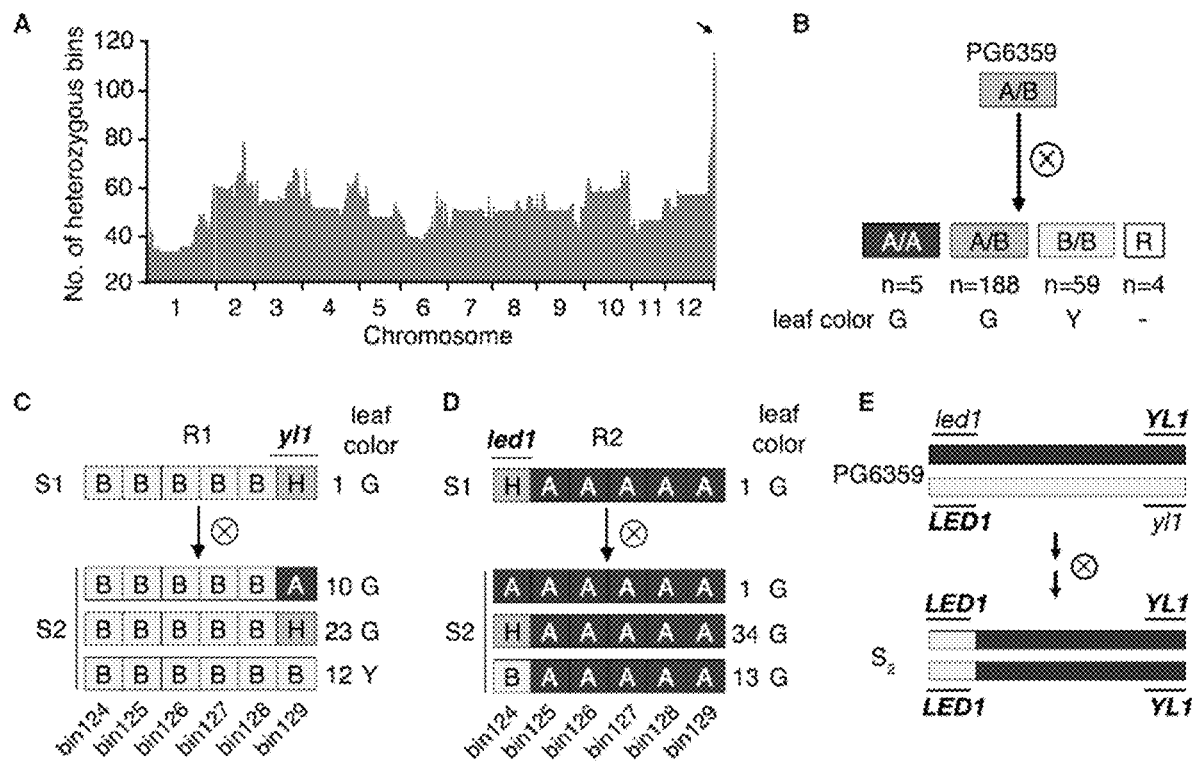

FIG. 4 illustrates breaking the close linkage of two deleterious mutations in repulsion phase. (A) Number of heterozygous bins in $S_2$ plants. (B) Segregation of the SD locus at the end of Chr. 12 in the $S_1$ population. R represents recombinants. (C)-(D) Genotype and phenotype segregation in the selfed progeny of recombinant R1 (C) and R2 (D). Numbers after the genotypes represent the $S_2$ individuals with the same genotype. G and Y in (B)-(D) represent green and virescent leaf color, respectively. (E) Obtaining the individuals with two beneficial alleles in the coupling phase. Dark grey box labeled "A" and light grey box labeled "B" in (B)-(E) indicate haplotypes A and B, respectively; medium grey box labeled "H" indicates heterozygous genotype.

Figure 5:
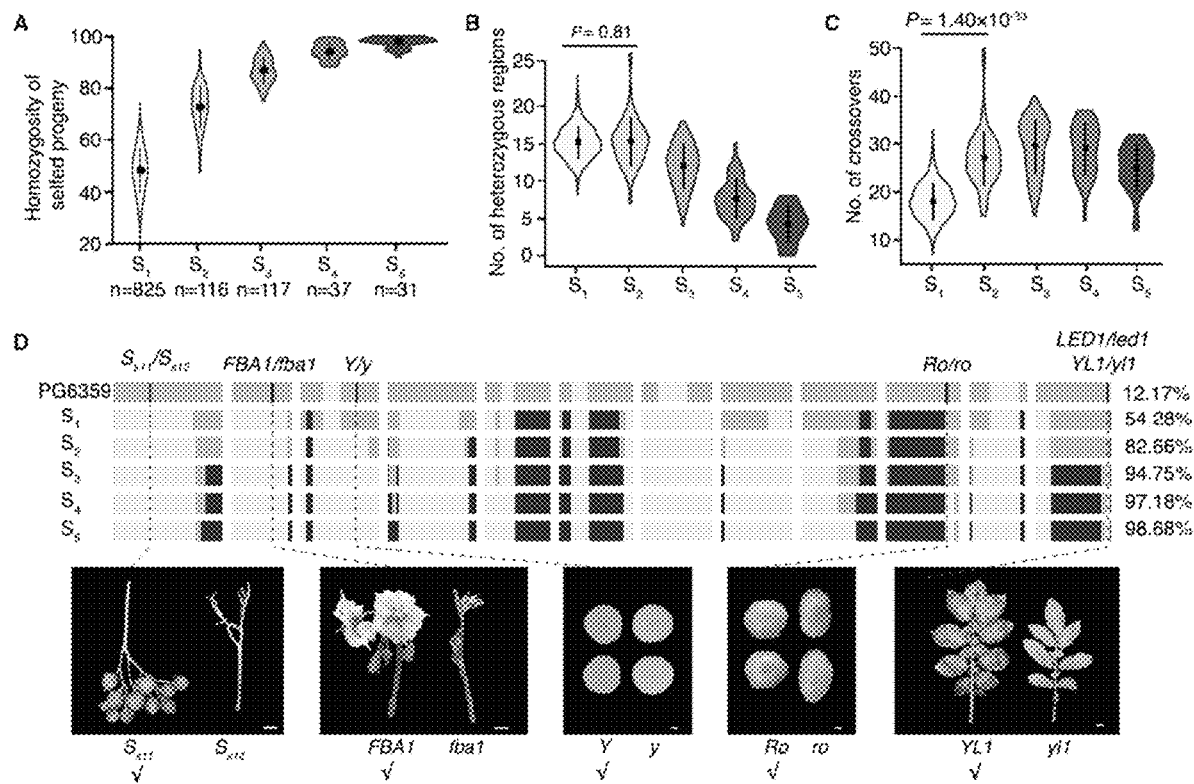

FIG. 5 illustrates the development of inbred lines using the heterozygous clone PG6359. (A) Genome-wide homozygosity of selfed progenies in different generations. (B) Numbers of heterozygous regions in different generations. (C) Number of detected crossovers in different generations. (D) Genomic changes of the inbred line "A6-10" in different generations. Numbers adjacent to the bars indicate genome homozygosity of each generation. Ticks represent the selected alleles, in selfed progeny. Scale bars represent 1 cm. Dark grey and light grey bars indicate the haplotypes A and B of PG6359, respectively, and medium grey bars represent heterozygote.

Figure 6:
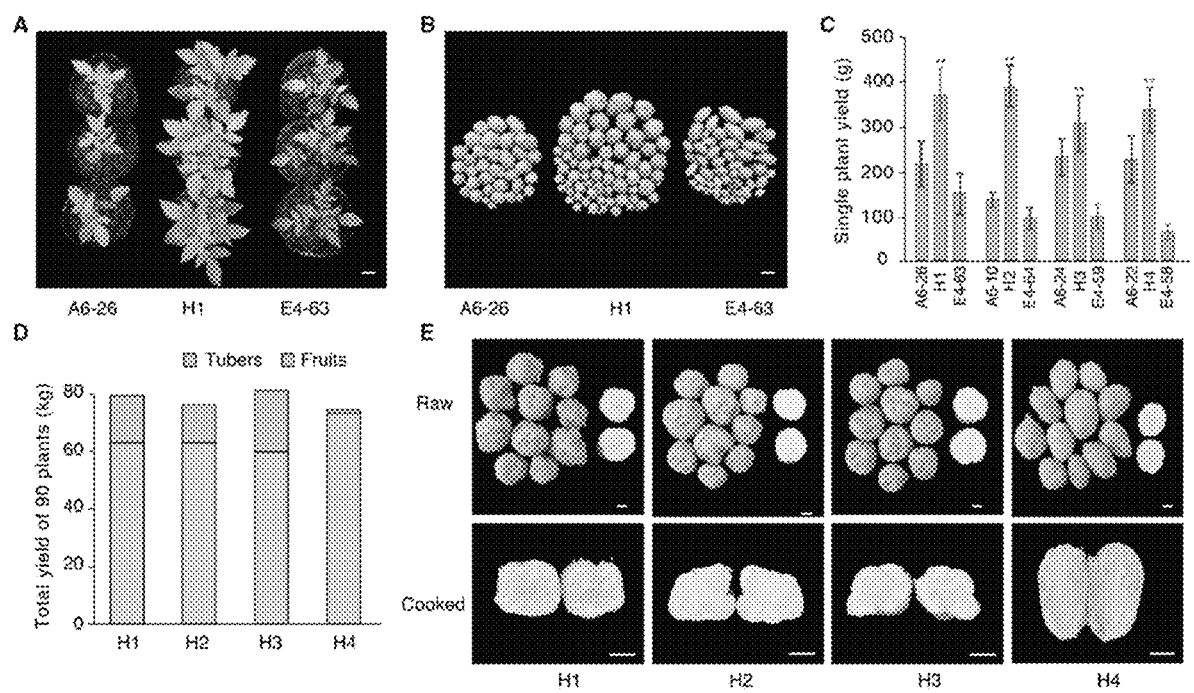

FIG. 6 illustrates that inbred-line-based $F_1$ hybrids exhibit strong heterosis. (A) Growth vigor of the $F_1$ hybrid H1 and its parents. (B) Tubers yield of the $F_1$ hybrid H1 and its parents. The tubers were harvested from three plants. Scale bars in (A) and (B) represent 2 cm. (C) Tuber weight of four $F_1$ hybrids and their parents. These plants were grown from seed and cultivated in pots in a greenhouse. The y-axis indicates the average tuber weight of twelve plants. Values are mean+SD, n=12 biological replicates. Asterisks represent significant differences between parental lines and $F_1$ hybrids determined by Student's t test. **p<0.01. (D) Total tuber (bottom bars) and fruit (top bars) weight of ninety plants for each $F_1$ hybrid. These plants were grown from mini-tubers, directly harvested from true-seed plants. (E) Tuber shape and flesh color (raw and cooked) of four $F_1$ hybrids. Scale bars=3 cm.

DETAILED DESCRIPTION

Potato (*Solanum tuberosum* L.) is a valuable non-grain food crop in the world, and increased potato productivity will help secure food supply for the increasing global population. Conventionally, cultivated potato is a tetraploid, highly heterozygous, and vegetatively propagated crop. The tetraploid genetics and heterogeneity in the genome has hampered genetic improvement of potato varieties. When potatoes are reproduced vegetatively from tuber clones, it can present logistic difficulties because tubers are bulky and perishable to transport and plant, and can quickly degenerate when pressured by disease. Hybrid diploid potato propagated by seed, in contrast, provides a solution in addressing these issues and offers further benefits in improving genetic gains and yield performance.

However, hybrid potato breeding has long been considered as being impracticable. To make a hybrid of sufficient heterosis and uniformity, the two parental lines require high genome homozygosity, adequate vigor and fertility, and a reasonable degree of genetic divergence. In this regard, there are two major obstacles to be overcome. The first obstacle lies in the fact that most diploid lines are self-incompatible. A recent work was the discovery and introgression of the S-locus inhibitor (Sli) gene, from the wild species *S. chacoense*, a dominant locus that renders self-compatibility in diploid potato, making selfing possible (Hosaka and Hanneman Jr., 1998). Alternative solutions include using genome editing to knock out the S-RNase gene, a major determinant of self-incompatibility (Enciso-Rodriguez et al., 2019; Ye et al., 2018) and searching for natural mutants of S-RNase (Zhang et al., 2019). More difficult to solve is the second obstacle, inbreeding depression, mainly caused by deleterious recessive alleles, whose detrimental effects would be exposed through selfing (Charlesworth and Willis, 2009). Thus, elimination of deleterious mutations is crucial for development of pure inbred lines. Yet, even in a self-compatible diploid clone, purging of deleterious mutations, to obtain a highly homozygous inbred line, is not straightforward as expected. After the initial successful conceptual test of hybrid potato breeding (Lindhout et al., 2011), over the ensuing decade of selfing and selection, the homozygosity of inbred lines remained low. Recently, a self-compatible diploid inbred line, termed "Solyntus", was de novo assembled, but unfortunately, >20% of the Solyntus genome is still heterozygous, even for this $F_9$ inbred line (van Lieshout et al., 2020). In practical breeding, 20% of genome heterozygosity means too many traits will be segregating; hence, this low homozygosity will limit the uniformity and commercialization of any resultant $F_1$ hybrids (Stokstad, 2019). Clearly, these outcomes indicate that the conventional selfing and selection approach, as a breeding strategy, is ineffective in achieving the highly anticipated breeding outcomes.

Accordingly, the present disclosure is based on the surprising results that methods disclosed herein have been found to produce diploid, fertile, self-compatible inbred potato materials with superior homozygosity. These highly homozygous diploid inbred potato materials, when used as parental lines, have been found to produce hybrid diploid potatoes with high levels of heterosis and uniformity. Provided herein are materials and methods for developing pure inbred lines and vigorous $F_1$ hybrids using advanced genetics and breeding techniques, e.g., genome design, which applies genome analyses for decision making in the entire process of inbred line development and creation of $F_1$ hybrids.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown but are to be accorded the scope consistent with the claims.

All references, including publications, patent applications, and patents, cited herein are hereby incorporated by reference to the same extent as if each reference were individually and specifically indicated to be incorporated by reference and were set forth in its entirety herein.

Definitions

The terminology used in the description of the various described embodiments herein is for the purpose of describing particular embodiments only and is not intended to be limiting.

The term "potato" is used herein to refer to material that is essentially of species *Solanum tuberosum*, but may include introgression segments of other tuber bearing *Solanum* species such as *Solanum chacoense*, *Solanum phureja*, *Solanum andigena*, and *Solanum demissum*.

The term "potato plant" is used herein to refer to a seedling or mature plant as grown from cell culture or seed. Persons of ordinary skill in the art will recognize that when the term "potato plant" is used in the context of the present disclosure, this also includes derivative varieties that retain the essential distinguishing characteristics of for instance potato varieties that are subject of the present disclosure, such as a Single Gene Converted plant of that variety or a transgenic derivative having one or more value-added genes incorporated therein (such as herbicide or pest resistance). Backcrossing methods can be used with the present disclosure to improve or introduce a characteristic into the variety.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. Crossing is widely used in plant breeding and results in a mix of genomic information between the two plants crossed one chromosome from the mother and one chromosome from the father. This will result in a new combination of genetically inherited traits. Usually, the progeny of a crossing is designated as: "$F_1$". If the $F_1$ is not uniform (segregates) it is usually designated as "$F_1$ population". "Selfing" of a homozygous plant will usually result in a genetic identical plant since there is no genetic variation. "Selfing" of an $F_1$ will result in an offspring that segregates for all traits that have heterozygotic loci in the $F_1$. Such offspring is designated: "$F_2$" or "$F_2$ population."

When referring to "crossing" in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

As used herein, the terms "introgressing", "introgress" and "introgressed" refer to both a natural and artificial process whereby individual genes or entire chromosomes are moved from one individual, species, variety or cultivar into the genome of another individual, species, variety or cultivar, by crossing those individuals, species, varieties or cultivars. In plant breeding, the process usually involves selfing or backcrossing to the recurrent parent to provide for an increasingly homozygous plant having essentially the characteristics of the recurrent parent in addition to the introgressed gene or trait.

The term "introgression" refers to the result of an introgression event.

The term "backcross" refers to the result of a "backcrossing" process wherein the plant resulting from a cross between two parental lines is (repeatedly) crossed with one of its parental lines, wherein the parental line used in the backcross is referred to as the recurrent parent. Repeated backcrossing results in replacement of genome fragments of the donor parent with those of the recurrent. The offspring of a backcross is designated "BCx" or "BCx population", where "x" stands for the number of backcrosses.

The term "backcrossing" as used herein refers to the repeated crossing of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene or a limited number of genes transferred from the nonrecurrent parent.

The term "selfing" refers to the process of self-fertilization wherein an individual is pollinated or fertilized with its own pollen. Repeated selfing eventually results in homozygous offspring.

A "line", as used herein, refers to a population of plants derived from a single cross, backcross or selfing. The individual offspring plants are not necessarily identical to one another. It is possible that individual offspring plants are not vigorous, fertile or self-compatible due to natural variability. However, it is foreseen that suitable plants that are vigorous, fertile and self-compatible can be easily identified in a line and used for additional breeding purpose.

As used herein, the term "allele(s)" means any of one or more alternative forms of a gene, all of which alleles relate to at least one trait or characteristic. In a diploid cell or organism, the two copies of a gene occupy corresponding loci on a pair of homologous chromosomes. Each copy may be a distinct allele.

A "gene" is defined herein as a hereditary unit (often indicated by a sequence of DNA) that occupies a specific location on a chromosome and that contains the genetic instruction for a contribution to potential phenotypic characteristics or trait in a plant.

A "locus" is defined herein as the position that a given gene occupies on a chromosome of a given plant species.

As used herein, the term "homozygous" means a genetic condition existing when identical alleles reside at corresponding loci on homologous chromosomes.

Homozygosity levels are average values for the population, and refer preferably to those loci wherein the parents differ.

As used herein, the term "heterozygous" means a genetic condition existing when different alleles reside at corresponding loci on homologous chromosomes.

As used herein, the term "progeny" means (a) genetic descendant(s) or offspring.

As used herein, the term "population" means a genetically heterogeneous collection of plants sharing a common genetic derivation.

As used herein, the term "hybrid" means any offspring of a cross between two genetically unlike individuals, more preferably the term refers to the cross between two (elite or inbred) breeding lines which will not reproduce true to the parent from seed.

The term "breeding line", as used herein, refers to a line of a cultivated potato having commercially valuable or agronomically desirable characteristics, as opposed to wild varieties or landraces. The term includes reference to an elite breeding line or elite line, which represents an essentially homozygous, usually inbred, line of plants used to produce commercial $F_1$ hybrids. An elite breeding line is obtained by breeding and selection for superior agronomic performance comprising a multitude of agronomically desirable traits. An elite plant is any plant from an elite line. Superior agronomic performance refers to a desired combination of agronomically desirable traits as defined herein, wherein it is desirable that the majority, preferably all of the agronomically desirable traits are improved in the elite breeding line as compared to a non-elite breeding line. Elite breeding lines are essentially homozygous and are preferably inbred lines.

The term "elite line", as used herein, refers to any line that has resulted from breeding and selection for superior agronomic performance. An elite line preferably is a line that has multiple, preferably at least 3, 4, 5, 6 or more (genes for) desirable agronomic traits as defined herein.

The terms "cultivar" and "variety" are used interchangeable herein and denote a plant with has deliberately been developed by breeding, e.g., crossing and selection, for the purpose of being commercialized, e.g., used by farmers and growers, to produce agricultural products for own consumption or for commercialization (fresh consumption, processing, feed, etc.). The term "breeding germplasm" denotes a plant having a biological status other than a "wild" status, which "wild" status indicates the original non-cultivated, or natural state of a plant or accession.

As used herein, the terms "purebred", "pure inbred" or "inbred" are interchangeable and refer to a substantially homozygous plant or plant line obtained by repeated selfing and-or backcrossing.

As used herein, the term "essentially derived variety" (EDV) refers to a variety having one, two, three or more physiological and/or morphological characteristics that are different from the "initial" or "original" variety/line, but otherwise having all the physiological and morphological characteristics of the initial or original variety/line from which it is derived.

As used herein, the term "molecular genetic marker" or short "marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion/deletion (INDEL) mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, the term "plant part" indicates a part of the potato plant, including organelles, single cells and cell tissues such as plant cells that are intact in plants, cell clumps and tissue cultures from which potato plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, calli, and the like.

Unless expressly stated otherwise, the term "seed", as used throughout this specification, refers to the body from which a new plant develops (or kernel in some plants) containing the small embryonic plant enclosed in a seed coat covering, usually together with some stored food. This seed, referred to as botanical or "true" seed is the product of the ripened ovule of gymnosperm and angiosperm plants which occurs after fertilization and some growth within the mother plant.

As used herein the terms "vigor" and "vigorous" refer to the relative amount of above-ground or below-ground tissues of a plant, which relative amount may be more or less independent of one another.

Tuber yield, unless expressly stated otherwise, is based on the tubers formed from a seedling plant, in contrast to the tubers formed from a tuber-grown plant-which yield may be 50-200% more than the yield of a seedling.

The term "diploid" as used herein refers to a plant wherein each vegetative cell contains two sets of chromosomes ($2x=2n$, wherein n is the number of chromosomes). One set of chromosomes is donated from each parent.

The term "tetraploid" as used herein refers to a plant wherein each vegetative cell contains four sets of chromosomes ($2x=4n$).

The term "nematode resistance" as used herein refers to a plant in which a functional resistance gene has been introgressed that prevents the multiplication of at least one nematode population or isolate.

The term "disease resistance" as used herein refers to the ability to show more than 50% reduction of the amount of diseased leaf surface or tuber volume, or the amount of multiplication of an insect or pathogenic microorganism including but not limited to *Streptomyces* spp., *Rhizoctonia*, Silver scurf and, *Phytophthora infestans,*

The term "herbicide tolerance" as used herein refers to a plant which shows less than 50% damage of the foliage than the usual damage upon the application of a specified dosage of herbicide.

The term "cold tolerance" as used herein refers to the average amount of leaf surface of a plant which shows frost damage, which damage in cold tolerant plants is less than the average damage observed at a temp of minus 3° C. for relatively cold sensitive reference varieties such as e.g. Caribe and/or Kennebec.

The term "drought tolerance" as used herein refers to a plant which shows less than average damage at limiting water conditions as compared to relatively drought sensitive reference varieties such as Caribe and/or Carlton.

The term "flooding tolerance" as used herein refers to a 50% lower proportion of affected tubers (anaerobic degradation) relative to a plant which shows average damage at flooding.

The term "tolerance to wet rot" as used herein refers to a plant with the slightest level of resistance to *Erwinia* species (currently termed *Pectobacterium* spp.).

The term "tolerance to dry rot" as used herein refers to a plant with the slightest level of resistance to *Fusarium* species.

The term "salinity tolerance" as used herein refers to a plant which shows less damage than average at salinity conditions.

The term "growth rate" as used herein refers to the increase of plant biomass per unit of time.

The term "tuber development defects" (e.g. misshapen or damaged tubers)" as used herein refers to a plant which shows visual as well as internal malformations of tubers during plant development and/or tuber harvest.

The term "tuber yield" as used herein refers to the total weight of tubers of a plant or of a population of plants generally expressed in grams of fresh weight.

The term "tuber size" as used herein refers to the absolute width, height and length of a tuber. Beneficial tuber sizes include plant-average tuber sizes of about 80-160 grams per tuber. Mean tuber number for commercially valuable plants are about 8-12 tubers per plant.

The term "tuber skin color" as used herein refers to the color of the skin of a tuber after harvest as the result of anthocyanin accumulation in tuber skin tissues.

The term "eye depth" as used herein refers to the relative distance between the skin surface and the shoot primordium of a tuber.

The term "tuber shape" as used herein refers to the length/width ratio, to indicate the continuous variation from round, oval to long tuber shapes, as well as the height/width ratio, to indicate the continuous variation from cylindrical to the amount of flatness of a tuber.

The term "tuber flesh color" as used herein refers to the color of the interior of the tuber flesh after harvest as the result of the absence or presence of carotenoid compounds causing white or yellow flesh color, respectively, as well as the absence of anthocyanins compounds causing red, blue, purple shades of flesh color, irrespective of the presence of color in patterns being partial or full.

The term "tuber taste" as used herein refers to the consumers' appreciation by consuming a cooked potato tuber.

The term "tuber shelf life" and "tuber storage ability" as used herein are synonymous and refer to lack of changes in appearance of a tuber at storage.

The term "tuber dormancy period" as used herein refers to the time period between sowing and sprouting of a tuber, while sown at normal conditions.

The term "resistance to tuber dehydration" as used herein refers to a plant with shows less dehydration of the tuber than average at low humidity conditions (see shelf life).

The term "tuber starch content" as used herein refers to the starch weight over the total fresh weight of a tuber.

The term "tuber dry matter content" as used herein refers to the weight of the dry components of a potato divided over the total fresh weight.

The term "tuber cooking quality" as used herein refers to the continuous variation from firm to mealiness of a tuber after cooking.

The term "tuber frying quality" as used herein refers to the consumers' appreciation of a tuber after frying.

The term "tuber chip making quality" as used herein refers to the consumers' appreciation of a tuber after making chips.

The term "tuber uniformity" as used herein refers to the standard deviation of tuber traits, whereby a low standard variation refers to high uniformity and vice versa.

The term "cold sweetening resistance" as used herein refers to resistance of a tuber to produce glucose and/or fructose while stored at temperatures below 8° C.

The term "tetraploid" as used herein refers to a plant wherein each vegetative cell contains four sets of chromosomes (4n). The terms "fertile" and "fertility" broadly refer to the capacity to reproduce, i.e., to conceive and to produce offspring, preferably fertile offspring. Thus, the term fertility refers to individuals that can be crossed to produce fertile offspring in that the flowers, when pollinated produce berries that contain seeds which when sown result in a plant that itself carries fertile flowers, etc.

The term "fertile offspring" or "fertile seed" is defined herein as seed capable of growing into a flower-producing potato plant wherein flowers are male and female fertile. Thus, the term preferably refers to a plant or seed that when grown into a plant is capable of producing offspring as male and as female parent by virtue of the presence of fertile ovules and fertile pollen (i.e., both male and female flowers are fertile).

The term "fertile plant" is defined herein as a plant capable of producing fertile seed carrying berries. Preferably said berries each carry at least 5, more preferably at least 15-20, even more preferably at least 50 fertile seed, still more preferably between 50 and 500 seeds.

The term "self-compatible" refers to capacity to develop seeds in berries that are the result of self-pollination, self-fertilization and producing fertile progeny.

For other terms as used herein, reference is made to Allard, R. W. Principles of Plant Breeding, 2nd Edition, Wiley New York, 1999, and specifically to the Glossary therein.

As used in the description of the various described embodiments and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes", "including", "comprises", and/or "comprising", when used in this specification, specify the presence of stated features, integers, steps, operations, elements, and/or components, but do not preclude the presence or addition of one or more other features, integers, steps, operations, elements, components, and/or groups thereof. The term "if" is, optionally, construed to mean "when" or "upon" or "in response to determining" or "in response to detecting", depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]", depending on the context.

Although the following description uses terms "first", "second", etc., to describe various elements, these elements should not be limited by the terms. These terms are only used to distinguish one element from another. For example, a first potato line could be termed a second potato line, and, similarly, a second potato line could be termed a first potato line, without departing from the scope of the various described embodiments. The first potato line and the second potato line are both potato lines, but they are not the same potato lines.

Materials for Hybrid Potato Production

Accordingly, the present disclosure provides potato materials useful for hybrid breeding and production.

Inbred Potato Lines

In one aspect, the present disclosure provides a diploid, fertile, self-compatible inbred potato line, which can be used as a parent line for producing hybrid potato varieties.

In some embodiments, the potato inbred line has a designation of "A6-10". A representative sample of the seeds of "A6-10" has been deposited according to the Budapest Treaty in the China Center for Type Culture Collection (CCTCC), located at the College of Life Sciences, Wuhan University, Wuhan, Hubei 430072, China. Further details of the deposit may be referred to the Deposit Information section of the disclosure.

In some embodiments, the potato inbred line has a designation of "E4-63" or "E4-64". A representative sample of the seeds of "E4-63" or "E4-64" has been deposited according to the Budapest Treaty in the China Center for Type Culture Collection (CCTCC), located at the College of Life Sciences, Wuhan University, Wuhan, Hubei 430072, China. Further details of the deposit may be referred to the Deposit Information section of the disclosure.

Diploid Potatoes

Conventional cultivated potato varieties are tetraploid (2n=4x=48), in which a somatic (i.e., non-germline) cell has 4 homologous sets of chromosomes with each set containing 12 chromosomes.

In some embodiments, the present disclosure provides diploid potatoes (2n=2x=24), in which a somatic cell has 2 homologous sets of chromosomes with each set containing 12 chromosomes.

Genome Homozygosity

Obtaining a highly homozygous inbred line is not straightforward as expected. For instance, after the initial conceptual test of hybrid potato breeding (Lindhout et al., 2011), over the ensuing decade of selfing and selection, the homozygosity of inbred lines remained low. Recently, a self-compatible diploid inbred line, termed "Solyntus", was de novo assembled, but unfortunately, >20% of the Solyntus genome is still heterozygous, even for this F9 inbred line (van Lieshout et al., 2020). In practical breeding, 20% of genome heterozygosity means too many traits will be segregating; hence, this low homozygosity will limit the uniformity and commercialization of any resultant $F_1$ hybrids (Stokstad, 2019).

Accordingly, in one aspect of the present disclosure, provided herein is an inbred diploid potato line, wherein the inbred diploid potato line is fertile, self-compatible, and has at least 90% of genome homozygosity.

Homozygosity refers to a genetic state when identical alleles reside at corresponding loci on homologous chromosomes. By way of example, if two alleles at a genomic locus are identical (i.e., 100% similar) for both copies of chromosomes in a diploid line, the genomic locus is deemed homozygous. When all genomic loci are homozygous, the diploid line is deemed having 100% genome homozygosity.

In some embodiments, the inbred diploid potato line provided herein has at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of genome homozygosity.

In some embodiments, the inbred diploid potato line provided herein has 60-70%, 65-75%, 70-80%, 75-85%, 76-86%, 77-87%, 78-88%, 79-89%, 80-90%, 81-91%, 82-92%, 83-93%, 84-94%, 85-95%, 86-96%, 87-97%, 88-98%, 89-99%, 90-95%, 91-96%, 92-97%, 93-98%, 94-99%, 95-100%, 85-90%, 86-91%, 87-92%, 88-93%, or 89-94% of genome homozygosity.

Methods and techniques of determining if two alleles are identical or similar are known in the art. By way of example, allele identity/similarity can be determined via percentage (%) nucleotide sequence identity/similarity analysis, which refers to the percentage of nucleotide residues in a candidate sequence that are identical with the nucleotide residues in the specific nucleotide sequence, after aligning the sequences and introducing gaps, if necessary, to achieve the maximum percent sequence identity.

In some embodiments, alleles or genomic loci can be grouped into "bins" of certain length (e.g., 100 bp, 200 bp, 500 bp, 1 kb, 2 kb, 5 kb, 10 kb, 50 kb, 100 kb, 500 kb) for homozygosity analysis of the genome.

In some embodiments, the genome homozygosity is determined by the formula: (length of homozygous bins÷potato genome size)×100%.

Alignment for purposes of determining percent nucleotide sequence identity or homozygosity can be achieved in various ways that are within the skill in the art, for instance, using publicly available computer software such as BLAST, BLAST-2, CLUSTAL, ALIGN or MEGALIGN software. Those skilled in the art can determine appropriate parameters for measuring alignment, including any algorithms needed to achieve maximal alignment over the full length of the sequences being compared, as well as the size of the homozygous bins suited for the analysis.

Self-Compatibility

In still another aspect, provided herein is a diploid, fertile, and self-compatible potato line, wherein at least 85% of its genomic loci are in homozygous state, wherein the self-compatibility in the potato line is conferred by: 1) a low-expressed S-RNase allele $S_{S11}$ as found in potato clone "A6-10", representative seeds of which having been deposited with CCTCC under accession number P202204, or 2) a S-locus inhibitor (Sli) gene as found in potato clone "E4-63" or "E4-64", representative seeds of which having been deposited with CCTCC under accession number P202212 and P202220, respectively.

Self-incompatibility occurs commonly in tuber-bearing *Solanum* species, especially at the diploid level. The locus S with multiple alleles controls gametophytic self-incompatibility and has been found to locate on chromosome 1, which includes tightly linked S-RNase gene and SLF gene. A low-expressed S-RNase allele $S_{S11}$ has been identified to confer self-compatibility by Zhang et al. See, "The genetic basis of inbreeding depression in potato." Nat. Genet. (2019) 51, 374-378.

Accordingly, in some embodiments, the self-compatibility in the provided potato line is conferred by a low-expressed S-RNase allele $S_{S11}$.

A self-compatibility-inducing mutant gene, Sli, has also been identified to enable pure genetic lines to be established to study the breeding value of heterozygosity in potatoes (Hosaka and Hanneman 1998). The Sli gene was mapped at the distal end of chromosome 12; thus, the Sli gene is independent of the S locus.

Accordingly, in some embodiments, the self-compatibility in the provided potato line is conferred by an S-locus inhibitor (Sli) gene.

Accumulation of Beneficial Alleles and Purging of Deleterious Mutations

In some embodiments, the inbred diploid potato line disclosed herein comprises one or more beneficial alleles selected from the group consisting of an S-RNase S11 ($S_{S11}$) allele for self-compatibility, a Yellow Leaf 1 (YL1) allele for normal leaves, a Floral Bud Abortion 1 (FBA1) allele for fertility, and a Yellow (Y) allele for yellow tuber flesh.

Despite its large genetic variation regarding yield, harvest index, and water use efficiency, traditional potato breeding has attained only negligible advances in the most important breeding goals such as yield, tuber quality, and abiotic stress tolerance, and only modest progress in pathogen resistance. This low level of improvement has been attributed to the complexity of breeding a heterozygous tetraploid outbreeder rather than to the lack of genetic potential available in wild and cultivated material. Specifically, the tetraploid nature and vegetative propagation of conventional potato varieties are postulated to result in accumulation of deleterious mutations/alleles ("genetic load"), which would lead to severe inbreeding depression upon selfing of such varieties.

Accumulation of deleterious mutations may negatively impact various aspects of potato growth and development, including, e.g., self-compatibility, leaf chlorophyll development, fertility, yield, carotenoid content in tuber. Non-limiting examples of deleterious mutations or alleles include, yellow leaf 1 (yl1) that leads to leaf yellowing ("chlorosis"), floral bud abortion 1 (fba1) that leads to abortion of floral buds before flowering, and large-effect deleterious mutation 1 (led1) that negatively impacts the survival of homozygotes. Conforming to genetic nomenclature convention, deleterious mutations and alleles are typically notated in lower case.

Beneficial alleles, on the contrary, refer to the genes, mutations, or alleles that would positively impact potato growth and development that result in favorable traits for potato breeding and production. Genetic variation may provide a gene with both a beneficial allele and a deleterious allele. In those cases, favorable alleles are typically notated in upper case or capitalized. For example, a Yellow Leaf 1 (YL1) allele leads to development of normal green leaves, a Floral Bud Abortion 1 (FBA1) allele leads to fertile flowers, and a Yellow (Y) allele leads to yellow tuber flesh, and Large-Effect Deleterious Mutation 1 (LED1) allele leads to survival of homozygotes.

In some embodiments, the present disclosure provides an inbred diploid potato line that has deleterious mutations purged and beneficial alleles accumulated as compared to a control line, such as a conventional potato line that has not been improved using the methods of present disclosure.

In some aspect, provided herein is an inbred diploid potato line, comprising a beneficial Yellow Leaf 1 (YL1) allele and a beneficial Large-Effect Deleterious Mutation 1 (LED1) allele in the coupling phase (e.g., genetically linked, on the same chromosome).

Essentially Derived Variety (EDV)

In still another aspect, provided herein is an essentially derived variety (EDV) of the inbred potato line disclosed herein.

By way of example, a potato variety/clone/line may be deemed to be essentially derived (i.e., an EDV) from an inbred potato line disclosed herein (the "initial variety"), if it meets the following: (i) it is predominantly derived from the initial variety, or from a variety that is itself predominantly derived from the initial variety, while retaining the expression of essentially all characteristics that result from the genotype or combination of genotypes of the initial variety; and (ii) it is clearly distinguishable from the initial variety (e.g., one, one or more, two, two or more, three, three or more characteristics are different from the initial variety); and (iii) except for the differences which result from the act of derivation, it conforms to the initial variety in the expression of the essential characteristics that result from the genotype or combination of genotypes of the initial variety. Thus, an EDV may be obtained, for example, by the selection of a natural or induced mutant or of a somaclonal variant, the selection of a variant individual from plants of the initial variety, backcrossing, or transformation by genetic engineering. Such a variant may be selected at any time, e.g., in the field or greenhouse, during breeding, during or after in vitro culture of cells or tissues, during regeneration of plants.

In some embodiments, provided herein is an essentially derived variety (EDV) of the inbred potato line disclosed herein, wherein the EDV has one, two, or three physiological and/or morphological characteristics that are different from the inbred potato line, but otherwise having all the physiological and morphological characteristics of the inbred potato line.

In some embodiments, the EDV is a Single Gene Converted plant of a potato inbred line disclosed herein, or a transgenic derivative having one or more value-added genes incorporated therein (such as herbicide or pest resistance). Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. Transgenes can be introduced into the plant using any of a variety of established recombinant methods well-known to persons skilled in the art. See, for example, Miki et al. (1993).

An EDV may also be determined by its genome sequence similarity with the initial variety. For instance, the genome of an EDV of an potato inbred line disclosed herein may have at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence similarity with the genome of the potato inbred line disclosed herein.

In some embodiments, provided herein is an essentially derived variety (EDV) of the inbred potato line disclosed herein, wherein the EDV is a clone/line/variety derived from the inbred potato line "A6-10" as deposited under CCTCC accession number P202204, the inbred potato line "E4-63" as deposited under CCTCC accession number P202212, or the inbred potato line "E4-64" as deposited under CCTCC accession number P202220, wherein at least 75% of the EDV's genome or genotype is present in the genome or genotype of "A6-10", "E4-63", or "E4-64".

Hybrid Potato Lines

In some aspect, provided herein is an $F_1$ hybrid progeny produced from the inbred diploid potato lines.

Hybrid Vigor and Uniformity

Hybrid crops, compared to their inbred counterparts, are more vigorous, faster-growing, and uniform—a phenomenon known as "hybrid vigor" or "heterosis". The disclosed $F_1$ hybrid potato line, for example, exhibits more robust and uniform performance relative to its parents, such as increased biomass, size, yield, growth rate, or fertility.

Past effects of producing hybrid potato varieties have been less than satisfactory. Without wishing to be bound by any theory, it is postulated that the successful creation of the hybrid potato in the present disclosure is due to the use of the inbred diploid potato lines having a high level of genome homozygosity, accumulation of beneficial alleles, and/or absence of deleterious alleles as described above.

By way of example, the present disclosure provides an $F_1$ hybrid diploid potato line having two parental inbred potato lines, wherein each of the two parental inbred lines has a genome homozygosity of at least 90%, wherein the genome homozygosity is determined by the formula: (length of homozygous bins÷potato genome size)×100%. In some embodiments, each of the two parental inbred lines has a genome homozygosity of at least 80%, at least 85%, at least 90%, at least 91%, at least 92%, at least 93%, at least 94%, at least 95%, at least 96%, at least 97%, at least 98%, at least 99%, or 100%.

In some embodiments, the $F_1$ hybrid potato line disclosed herein exhibits a high level of heterosis or hybrid vigor. The degree of heterosis or hybrid vigor may be calculated as the difference in the phenotypic performance of a trait between a hybrid and the average of its two distinct parents. In some embodiments of the $F_1$ hybrid potato line disclosed herein, the tuber yield of the $F_1$ hybrid is at least 30% higher than the average tuber yield of the two parental lines grown in the field. In some embodiments, the tuber yield of the $F_1$ hybrid is at least 10%, at least 20%, at least 30%, at least 40%, at least 50%, at least 60%, at least 70%, at least 80%, at least 90%, or at least 100% higher than the average tuber yield of the two parental lines grown in the field.

In some embodiments of the $F_1$ hybrid potato line disclosed herein, the hybrid potato line has a tuber yield of at least 250 grams per plant. In some embodiments, the hybrid potato line has a tuber yield of at least 100 grams, at least 150 grams, at least 200 grams, at least 250 grams, at least 300 grams, at least 350 grams, at least 400 grams, at least 450 grams, at least 500 grams, at least 600 grams, at least 700 grams, at least 800 grams, at least 900 grams, or at least 1000 grams per plant.

In some embodiments, the $F_1$ hybrid potato line disclosed herein exhibits a high level of uniformity. The degree of uniformity may be represented by a standard deviation of a measurable trait from the hybrid potato line. For example, in some embodiments, the hybrid potato line has a standard deviation of less than 5 grams, less than 10 grams, less than 15 grams, less than 20 grams, less than 25 grams, less than 30 grams, less than 35 grams, less than 40 grams, less than 45 grams, less than 50 grams, less than 55 grams, less than 60 grams, less than 65 grams, less than 70 grams, less than 75 grams, less than 80 grams, less than 85 grams, less than 90 grams, less than 95 grams, or less than 100 grams in its tuber yield or a subgroup of the tuber yield (e.g., small tubers, medium tubers, large tubers) per plant. The degree of uniformity may also be represented by a coefficient of variation (CV, ratio of the standard deviation of all values to the mean value) of a measurable trait from the hybrid potato line. For example, in some embodiments, the hybrid potato line has a CV of less than 1%, less than 2%, less than 3%, less than 4%, less than 5%, less than 6%, less than 7%, less than 8%, less than 9%, less than 10%, less than 15%, less than 20%, less than 25%, less than 30%, less than 35%, less than 40%, less than 45%, or less than 50% in its tuber yield or a subgroup of the tuber yield (e.g., small tubers, medium tubers, large tubers) per plant.

Complementation

Via hybridization, genes/alleles from the two parents may complement or interact to achieve an additive or a synergistic effect in the resulting hybrid. For instance, in some embodiments, provided herein is an $F_1$ hybrid diploid potato line produced from two parental inbred potato lines, wherein the two parental inbred lines comprise different self-compatibility genes. For example, one inbred parent comprises a low-expressed S-RNase $S_{S11}$ gene, and the other inbred parent comprises an S-locus inhibitor (Sli) gene. As a result, the $F_1$ hybrid exhibits stable fertility.

Traits

In some embodiments, the potato line disclosed herein comprises at least one agronomically desired trait selected from the group consisting of strong growth vigor, high yield, improved nutritional value, insect tolerance, nematode resistance, disease resistance, herbicide tolerance, cold tolerance, drought tolerance, wet tolerance, tolerance to dry and wet rot, salinity tolerance, and cold-sweetening resistance.

In some embodiments of the potato line disclosed herein, the potato line produces tubers having a carotenoid content of at least 5 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, at least 50 mg/kg, at least 60 mg/kg, at least 70 mg/kg, at least 80 mg/kg, at least 90 mg/kg, or at least 100 mg/kg per dry weight.

In some embodiments of the potato line disclosed herein, the potato line produces tubers having a dry matter percentage of at least 10%, at least 15%, at least 20%, at least 25%, at least 30%, at least 35%, at least 40%, at least 45%, or at least 50%.

In some embodiments, the potato line produces tubers having a carotenoid content of at least 40 mg/kg dry-weight and/or a dry matter percentage of at least 20%.

Other Materials

In some aspect, provided herein is a plant of the potato line disclosed herein.

In some aspect, provided herein is a seed or a tuber of the plant disclosed herein.

In some aspect, provided herein is a plant part from the plant disclosed herein.

In some embodiments of the plant part disclosed herein, the plant part is a seed, a tuber, a leaf, a flower, a fruit, a cell, a tissue, an organ, or a portion thereof.

In still another aspect, provided herein is a tissue culture produced from a protoplast or a cell of the plant disclosed herein, wherein the protoplast or cell is derived from a plant part of the plant selected from the group consisting of leaf, pollen, embryo, cotyledon, hypocotyl, meristematic root cell, root tip, pistil, anther, ovule, flower, shoot, stem, seed, and petiole. Methods and techniques of establishing tissue culture are known in the art. See, e.g., Kamo et al. (1985), Duncan et al. (1985), and West et al. (1993).

In still another aspect, provided herein is a Single Gene Converted plant of a potato line disclosed herein, or a transgenic derivative having one or more value-added genes incorporated therein (such as herbicide or pest resistance). Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. Transgenes can be introduced into the plant using any of a variety of established recombinant methods well-known to persons skilled in the art. See, for example, Miki et al. (1993).

Methods for Hybrid Potato Production

A core mission of hybrid potato breeding is to develop highly homozygous inbred lines derived from different lineages. High residual heterozygosity, in inbred lines, will result in segregations in the $F_1$ hybrids, reducing their commercial quality. Accordingly, the present disclosure provides methods for producing highly vigorous and uniform potato hybrids that are valuable to commercial production.

Figure 1:
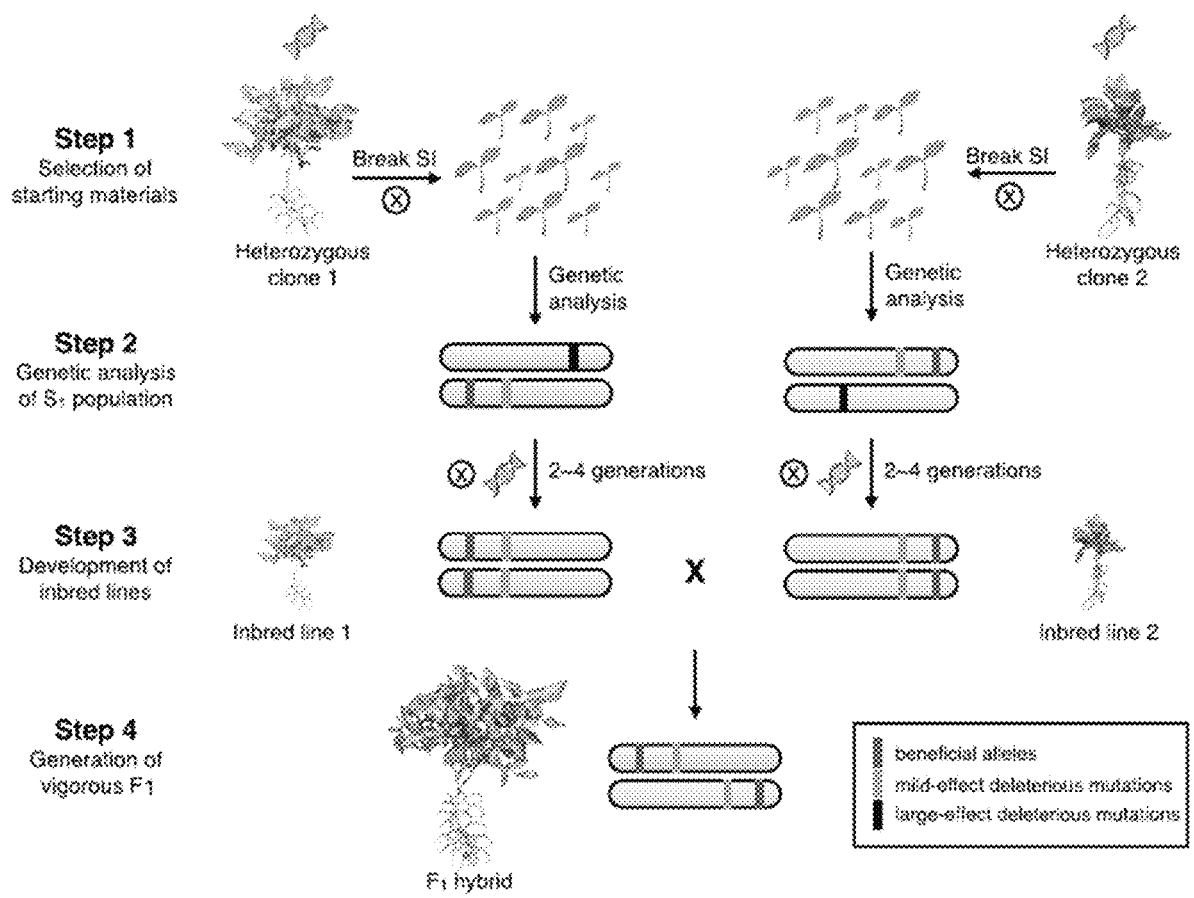
FIG. 1 illustrates a schematic diagram of genome design for hybrid potato breeding. This breeding pipeline includes four steps. Step 1 is to select the starting materials according to genome analysis and break self-incompatibility. Step 2 is to identify the deleterious (black) and beneficial (dark grey) alleles by genetic analysis of $S_1$ population. Step 3 is to develop inbred lines containing beneficial alleles. Step 4 is to create the vigorous $F_1$ hybrid by crossing two inbred lines with different genetic backgrounds.

An exemplary process for using the disclosed methods to produce pure inbred lines and vigorous $F_1$ hybrids is by means of genome design, which applies genome analyses for decision making in the entire process of inbred line development and creation of $F_1$ hybrids. FIG. 1 illustrates an exemplary pipeline for carrying out the disclosed hybrid potato production methods using genome design.

An exemplary process may involve the following four steps:
1) select or create, as starting materials, self-compatible diploid clones with low genomic heterozygosity;
2) analyze the $S_1$ population of this starting material to identify the segregation distortion regions (SDs) and genetic loci carrying large-effect deleterious mutations or controlling agronomic traits;
3) develop highly homozygous inbred lines, by continuous selfing and genome-assisted selection, to purge deleterious mutations and stack beneficial alleles; and
4) cross the inbred lines derived from different lineages to obtain $F_1$ hybrids which are then evaluated for performance.

Examples of the metrics used in the process include: the percentage of genome homozygosity and the number of deleterious mutations in the starting material, the number of segregation distortions in the $S_1$ population, the haplotype information to infer the break of tight linkage between beneficial and deleterious alleles, and the genome complementarity of the parental lines.

By way of example, in one aspect, provided herein is a method for producing $F_1$ hybrid potato seed, comprising: obtaining a first self-compatible diploid potato plant and a second self-compatible diploid potato plant; selfing the first self-compatible diploid potato plant to obtain a first progeny population and selfing the second self-compatible diploid potato plant to obtain a second progeny population; selecting from the first and second progeny populations one or more progeny potato plants having genome homozygosity of at least 60%; repeating steps (b) to (c) 2 to 4 times on the selected progeny plant in each of the first and second progeny populations to obtain inbred potato lines having at least 90% of genome homozygosity; and generating $F_1$ hybrid potato seed by crossing an inbred line from the first progeny population and an inbred line from the second progeny population.

In another example, provided herein is a method for producing $F_1$ hybrid potato seed, comprising: obtaining a first self-compatible diploid potato clone and a second self-compatible diploid potato clone; selfing the first self-compatible diploid potato clone to obtain a first progeny population and selfing the second self-compatible diploid potato clone to obtain a second progeny population; performing genetic analysis on the first and second progeny populations to identify deleterious mutations and beneficial alleles in the genomes of the progeny populations; using genome-assisted selection to select progeny lines having fewer deleterious mutations and more beneficial alleles in each of the first and second progeny populations; repeating steps (b) to (d) 2 to 4 times on the selected progeny lines in each of the first and second progeny populations to obtain inbred potato lines having at least 90% of genome homozygosity; and generating $F_1$ hybrid potato seed by crossing an inbred line from the first progeny population and an inbred line from the second progeny population.

Obtaining Starting Materials

In some embodiments, the method comprises a step of selecting or creating starting materials from which the inbred lines are developed.

Various suitable starting materials may be used with the disclosed methods. In some embodiments, the starting materials comprise a diploid potato clone as a starting material.

In some embodiments of the foregoing, the selecting or creating starting materials comprises evaluating the percentage of genome homozygosity and/or the number of deleterious mutations in the starting materials. In some embodiments, a starting material with low levels of genome heterozygosity and deleterious mutations are selected or created. In some embodiments, the starting material is selected or created with a level of genome heterozygosity less than 70%, less than 60%, less than 50%, less than 40%, less than 30%, less than 20%, less than 10%, or less than 5%.

In some embodiments of the foregoing, the selecting or creating starting materials comprises breaking self-incompatibility or introducing self-compatibility in a starting material.

Various methods of breaking self-incompatibility and introducing self-compatibility may be used with the disclosed methods. In some embodiments, a self-compatibility gene is introduced into the starting material. For example, the S-locus inhibitor (Sli) gene from the wild species *S. chacoense* can be introgressed into the starting material that renders self-compatibility in the starting material. For another example, genome editing is used to knock out the S-RNase gene as a way to introduce self-compatibility in the starting material. In some embodiments, a natural allele of S-RNase that has a low expression of the gene, e.g., the $S_{S11}$ allele, is introgressed into the starting material that renders self-compatibility in the starting material.

Genetic Analysis of Progeny

In some embodiments, the method comprises a step of genetically analyzing the progeny of the starting materials.

In some embodiments of the foregoing, the progeny is an $S_1$ population of the starting material, e.g., by selfing the starting material.

In some embodiments of the foregoing, the progeny is an $S_2$ population of the starting material, e.g., by selfing the $S_1$ progeny.

In some embodiments of the foregoing, the progeny is an $S_3$ population of the starting material, e.g., by selfing the $S_2$ progeny.

In some embodiments of the foregoing, the progeny is an $S_4$ population of the starting material, e.g., by selfing the $S_3$ progeny.

In some embodiments of the foregoing, the progeny is an $S_5$ population of the starting material, e.g., by selfing the $S_4$ progeny.

In some embodiments of the foregoing, the progeny is an S6 population of the starting material, e.g., by selfing the $S_5$ progeny.

In some embodiments, the analysis of progeny comprises analyzing progeny from at least 2, at least 3, at least 4, at least 5, or at least 6 generations of selfing from the starting materials.

In some embodiments of the method disclosed herein, the genome-assisted selection comprises reducing the number of deleterious mutations, breaking tight linkage of deleterious mutations, and/or stacking beneficial alleles in the genome.

In some embodiments, the genetic analysis comprises analyzing haplotype information to infer the break of tight linkage between beneficial and deleterious alleles.

In some embodiments of the method disclosed herein, the deleterious mutations and/or beneficial alleles are associated with gametic or zygotic survival, growth vigor, leaf chlorosis, flower development, fertility, tuber size, tuber number per plant, tuber shape, tuber flesh color, or a combination thereof.

Methods of identifying deleterious alleles and beneficial alleles are known in the art. See, e.g., Zhang et al. "The genetic basis of inbreeding depression in potato." Nat. Genet. 51 (2019): 374-378.

In some embodiments that may be combined with any of the foregoing, the genetic analysis comprises analyzing segregation distortions (SDs) in the progeny population, e.g., identifying and characterizing SDs therein. In some embodiments, the analysis of SDs is a genome-wide analysis of SDs. In some embodiments, the analyzed SDs are associated with large-effect deleterious alleles.

Distorted segregation (SD), the deviation of the observed genotypic ratios from the expected frequencies based on Mendel's laws of inheritance, is considered an evolutionary force primarily associated with genetic factors involved in reproduction and fitness. In general, the study of segregation distortion has been useful to screen and identify gametophytic mutants affecting male and female fertility in plants, as well as several hybrid sterility, hybrid weakness, and gametophytic competition genes acting as inter- or intraspecific reproductive barriers. SDs can often be associated with large-effect deleterious alleles.

Methods and techniques of detecting and calculating SDs are known in the art. For instance, a progeny population may be sequenced using a next-generation-sequencing (NGS) technique and the resulting sequencing data can be used to construct a linkage map, from which SDs may be calculated. See, e.g., Zhang et al. "The genetic basis of inbreeding depression in potato." Nat. Genet. 51 (2019): 374-378; Manrique-Carpintero et al. "Comparative analysis of regions with distorted segregation in three diploid populations of potato." G3: Genes, Genomes, Genetics 6.8 (2016): 2617-2628.

Development of Inbred Lines

To make a hybrid of sufficient heterosis and uniformity, the two parental lines require high genome homozygosity, adequate vigor and fertility, and a reasonable degree of genetic divergence.

In some embodiments, the method comprises a step of developing inbred lines.

In some embodiments, the developing of an inbred line comprises selecting a progeny plant from selfing the starting material, wherein the progeny plant contains desired beneficial alleles, lacks undesired deleterious alleles, has linkage between beneficial and deleterious alleles broken, and/or has a high level of genome homozygosity.

In some embodiments, the developed potato inbred line has a designation of "A6-10". A representative sample of the seeds of "A6-10" has been deposited according to the Budapest Treaty in the China Center for Type Culture Collection (CCTCC), located at the College of Life Sciences, Wuhan University, Wuhan, Hubei 430072, China.

In some embodiments, the developed potato inbred line has a designation of "E4-63". A representative sample of the seeds of "E4-63" has been deposited according to the Budapest Treaty in the China Center for Type Culture Collection (CCTCC), located at the College of Life Sciences, Wuhan University, Wuhan, Hubei 430072, China. Following the methods and threshold for determining heterozygosity used in van Lieshout et al., 2020 (e.g., a SNP rate of 200 SNPs per 30 Kbp as a threshold for heterozygosity), potato lines A6-10 and E4-63 exhibit 98.0% and 97.5%, respectively, genome homozygosity. This is higher than the 79.9% homozygosity observed for the F9 inbred reported in van Lieshout et al., 2020. Worth noting is that the genome-wide SNP-based homozygosity determination method in van Lieshout et al., 2020 is of higher resolution than the method used to determine homozygosity level in Lindhout et al., U.S. Pat. No. 11,140,841 (see Example 4 therein). The latter only relied on genotyping selected markers at a much lower density (e.g., using 24 marker loci to represent 24 chromosome arms, Lindhout asserted that 100% homozygosity was reached in two selfed generations). Similarly, the asserted population mean homozygosity level of 94% of F3 plants of U.S. Pat. No. 11,140,841 is in no way comparable to the high homozygosity observed in potato lines A6-10 and E4-63.

In some embodiments, the developed potato inbred line has a designation of "E4-64". A representative sample of the seeds of "E4-64" has been deposited according to the Budapest Treaty in the China Center for Type Culture Collection (CCTCC), located at the College of Life Sciences, Wuhan University, Wuhan, Hubei 430072, China.

In some embodiments, the developed potato inbred line has self-compatibility conferred by a low-expressed S-RNase allele $S_{S11}$.

In some embodiments, the developed potato inbred line has self-compatibility conferred by an S-locus inhibitor (Sli) gene.

In some embodiments, the developed potato inbred line comprises one or more beneficial alleles selected from the group consisting of an S-RNase S11 ($S_{S11}$) allele for self-compatibility, a Yellow Leaf 1 (YL1) allele for normal leaves, a Floral Bud Abortion 1 (FBA1) allele for fertility, and a Yellow (Y) allele for yellow tuber flesh.

In some embodiments, the developed potato inbred line comprises a beneficial Yellow Leaf 1 (YL1) allele and a beneficial Large-Effect Deleterious Mutation 1 (LED1) allele in the coupling phase.

In some embodiments, the developed inbred diploid potato line has at least 50%, at least 60%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of genome homozygosity.

In some embodiments of the foregoing, the selected progeny plant is further selfed for one or more generations to develop an inbred line.

Generation of $F_1$ Hybrids

In some embodiments, the method comprises a step of generating $F_1$ hybrids.

In some embodiments, the generating $F_1$ hybrids comprises crossing the developed inbred lines to obtain $F_1$ hybrids.

In some embodiments, the generating $F_1$ hybrids comprises choosing two developed inbred lines that have a desired level of difference in genetic backgrounds (e.g., genetic divergence in certain genomic loci) and crossing the two chosen inbred lines to obtain an $F_1$ hybrid.

In some embodiments, the generating $F_1$ hybrids comprises choosing two developed inbred lines that display a desired level of genome complementarity and crossing the two chosen inbred lines to obtain an $F_1$ hybrid.

In still another aspect, provided herein is a method for producing a hybrid potato seed, the method comprising crossing a first potato plant with a second potato plant and harvesting a hybrid potato seed resulting from the cross, wherein the first or second parent potato plant is derived from an inbred diploid potato line disclosed herein.

In still another aspect, provided herein is a method for producing a hybrid potato plant, the method comprising producing a seed according to the method disclosed herein, and growing the seed into a potato plant.

In still another aspect, provided herein is a method for producing a hybrid potato line, the method comprising: providing a first potato plant, wherein the first potato plant is a plant of potato line "A6-10", representative seeds of which having been deposited with CCTCC under accession number P202204; providing a second potato plant, wherein the second potato plant is a plant of potato line "E4-63" or "E4-64", representative seeds of which having been deposited with CCTCC under accession number P202212 and P202220, respectively; and cross-pollinating the first potato plant and the second potato plant to provide seeds and collecting the seeds to thereby provide a hybrid potato line.

In still another aspect, provided herein is a method for producing a vigorous $F_1$ hybrid potato line, the method comprising: providing a plurality of inbred potato lines; analyzing the genomes of the plurality of inbred potato lines to identify deleterious alleles and beneficial alleles in the genomes; calculating genome complementarity scores between the plurality of inbred potato lines based on the identified deleterious alleles and beneficial alleles in the genomes; selecting from the plurality of inbred potato lines a subset of inbred potato lines based on the calculated genome complementarity scores; and crossing the selected subset of inbred potato lines to obtain vigorous $F_1$ hybrid lines.

In some embodiments, the method further comprises growing the generated F1 hybrid potatoes to produce high-yield and uniform tubers.

EXAMPLES OF EMBODIMENTS

E1. A diploid, fertile, self-compatible inbred potato line selected from the group consisting of "A6-10", "E4-63", and "E4-64", representative seeds of which having been deposited at CCTCC under accession numbers P202204, P202212, and P202220, respectively.

E2. An inbred diploid potato line, wherein the inbred diploid potato line is fertile, self-compatible, and has at least 90% of genome homozygosity.

E3. A self-compatible and fertile inbred diploid potato line, having at least 90% of genome homozygosity.

E4. A diploid, fertile, and self-compatible potato line, wherein at least 85% of its genomic loci are in homozygous state,
wherein the self-compatibility in the potato line is conferred by: 1) a low-expressed S-RNase allele $S_{S11}$ as found in potato clone "A6-10", representative seeds of which having been deposited with CCTCC under accession number P202204, or 2) a S-locus inhibitor (Sli) gene as found in potato clone "E4-63" or "E4-64", representative seeds of which having been deposited with CCTCC under accession number P202212 and P202220, respectively.

E5. The inbred diploid potato line of any one of embodiments E2-E4, comprising one or more beneficial alleles selected from the group consisting of an S-RNase S11 ($S_{S11}$) allele for self-compatibility, a Yellow Leaf 1 (YL1) allele for normal leaves, a Floral Bud Abortion 1 (FBA1) allele for fertility, and a Yellow (Y) allele for yellow tuber flesh.

E6. An inbred diploid potato line, comprising a beneficial Yellow Leaf 1 (YL1) allele and a beneficial Large-Effect Deleterious Mutation 1 (LED1) allele in the coupling phase.

E7. An essentially derived variety (EDV) of the inbred potato line of any one of embodiments E1-E6.

E8. An $F_1$ progeny of the inbred potato line of any one of embodiments E1-E7.

E9. An $F_1$ hybrid diploid potato line having two parental inbred potato lines, wherein each of the two parental inbred lines has a genome homozygosity of at least 90%, wherein the genome homozygosity is determined by the formula: (length of homozygous bins÷potato genome size)×100%.

E10. An $F_1$ hybrid diploid potato line having two parental inbred potato lines, wherein the two parental inbred lines comprise different self-compatibility genes.

E11. The $F_1$ hybrid potato line of any one of embodiments E8-E10, wherein the tuber yield of the $F_1$ hybrid is at least 30% higher than the average tuber yield of the two parental lines grown in the field.

E12. The $F_1$ hybrid potato line of any one of embodiments E8-E11, wherein the hybrid potato line has a tuber yield of at least 250 grams per plant.

E13. The potato line of any one of embodiments E1-E12, comprising at least one agronomically desired trait selected from the group consisting of strong growth vigor, high yield, improved nutritional value, insect tolerance, nematode resistance, disease resistance, herbicide tolerance, cold tolerance, drought tolerance, wet tolerance, tolerance to dry and wet rot, salinity tolerance, and cold-sweetening resistance.

E14. The potato line of any one of embodiments E1-E13, wherein the potato line produces tubers having a carotenoid content of at least 40 mg/kg dry-weight and/or a dry matter percentage of at least 20%.

E15. A plant of the potato line of any one of embodiments E1-E14.

E16. A seed or a tuber of the plant of embodiment E15.

E17. A plant part from the plant of embodiment E15.

E18. The plant part of embodiment E17, wherein the plant part is a seed, a tuber, a leaf, a flower, a fruit, a cell, a tissue, an organ, or a portion thereof.

E19. A tissue culture produced from a protoplast or a cell of the plant of embodiment E15, wherein the protoplast or cell is derived from a plant part of the plant selected from the group consisting of leaf, pollen, embryo, cotyledon, hypocotyl, meristematic root cell, root tip, pistil, anther, ovule, flower, shoot, stem, seed, and petiole.

E20. A method for producing $F_1$ hybrid potato seed, comprising:
(a) obtaining a first self-compatible diploid potato plant and a second self-compatible diploid potato plant;

(b) selfing the first self-compatible diploid potato plant to obtain a first progeny population and selfing the second self-compatible diploid potato plant to obtain a second progeny population;
(c) selecting from the first and second progeny populations one or more progeny potato plants having genome homozygosity of at least 60%;
(d) repeating steps (b) to (c) 2 to 4 times on the selected progeny plant in each of the first and second progeny populations to obtain inbred potato lines having at least 90% of genome homozygosity; and
(e) generating $F_1$ hybrid potato seed by crossing an inbred line from the first progeny population and an inbred line from the second progeny population.

E21. A method for producing $F_1$ hybrid potato seed, comprising:
(a) obtaining a first self-compatible diploid potato clone and a second self-compatible diploid potato clone;
(b) selfing the first self-compatible diploid potato clone to obtain a first progeny population and selfing the second self-compatible diploid potato clone to obtain a second progeny population;
(c) performing genetic analysis on the first and second progeny populations to identify deleterious mutations and beneficial alleles in the genomes of the progeny populations;
(d) using genome-assisted selection to select progeny lines having fewer deleterious mutations and more beneficial alleles in each of the first and second progeny populations;
(e) repeating steps (b) to (d) 2 to 4 times on the selected progeny lines in each of the first and second progeny populations to obtain inbred potato lines having at least 90% of genome homozygosity; and
(f) generating $F_1$ hybrid potato seed by crossing an inbred line from the first progeny population and an inbred line from the second progeny population.

E22. The method of embodiment E21, further comprising a genetic analysis of genome-wide segregation distortions (SDs) in the progeny populations.

E23. The method of any one of embodiments E21-E22, wherein the genome-assisted selection comprises reducing the number of deleterious mutations, breaking tight linkage of deleterious mutations, and/or stacking beneficial alleles in the genome.

E24. The method of any one of embodiments E21-E23, wherein the deleterious mutations and/or beneficial alleles are associated with gametic or zygotic survival, growth vigor, leaf chlorosis, flower development, fertility, tuber size, tuber number per plant, tuber shape, tuber flesh color, or a combination thereof.

E25. A method for producing a hybrid potato seed, the method comprising crossing a first potato plant with a second potato plant and harvesting a hybrid potato seed resulting from the cross, wherein the first or second parent potato plant is derived from an inbred diploid potato line of any one of embodiments E1 to E7.

E26. A method for producing a hybrid potato plant, the method comprising producing a seed according to the method of embodiment E25, and growing the seed into a potato plant.

E27. A method for producing a hybrid potato line, the method comprising:
(a) providing a first potato plant, wherein the first potato plant is a plant of potato line "A6-10", representative seeds of which having been deposited with CCTCC under accession number P202204;
(b) providing a second potato plant, wherein the second potato plant is a plant of potato line "E4-63" or "E4-64", representative seeds of which having been deposited with CCTCC under accession number P202212 and P202220, respectively; and
(c) cross-pollinating the first potato plant and the second potato plant to provide seeds and collecting the seeds to thereby provide a hybrid potato line.

E28. A method for producing a vigorous $F_1$ hybrid potato line, the method comprising:
(a) providing a plurality of inbred potato lines;
(b) analyzing the genomes of the plurality of inbred potato lines to identify deleterious alleles and beneficial alleles in the genomes;
(c) calculating genome complementarity scores between the plurality of inbred potato lines based on the identified deleterious alleles and beneficial alleles in the genomes;
(d) selecting from the plurality of inbred potato lines a subset of inbred potato lines based on the calculated genome complementarity scores; and
(e) crossing the selected subset of inbred potato lines to obtain vigorous $F_1$ hybrid lines.

EXAMPLES

The examples described herein are offered to illustrate provided embodiments and are not intended to limit the scope of the present disclosure.

The following examples collectively illustrate an exemplary pipeline to carry out potato hybrid breeding by genome design (FIG. 1). This pipeline involved four steps, with the first being to select or create, as starting materials, self-compatible diploid clones with low genomic heterozygosity. The second step involved analysis of the $S_1$ population of this starting material to identify the segregation distortion regions (SDs) and genetic loci carrying large-effect deleterious mutations or controlling agronomic traits. Next, it was critical to develop highly homozygous inbred lines, by continuous selfing and genome-assisted selection, to purge deleterious mutations and stack beneficial alleles. Finally, the inbred lines derived from different lineages were crossed to obtain $F_1$ hybrids which are then evaluated for performance.

Example 1: Selection of Starting Materials

This example illustrates the first step of hybrid diploid potato breeding by genome design: selecting or creating, as starting materials, self-compatible diploid clones with low genomic heterozygosity.

Methods and Materials

Four diploid potato accessions, *S. tuberosum* RH, *S. tuberosum* group Stenotomum PG6359 (the original CIP code is CIP705468) and CIP701165, *S. tuberosum* group Phureja CIP703767, were used for genetic analysis in this study. RH and PG6359 are two self-compatible clones (Zhang et al., 2019). CIP701165 and CIP703767 are self-incompatible, which were crossed with E172 (containing the S-locus inhibitor gene, Sli). Then the $F_1$ clones were back-crossed with female parents, and two $BC_1$ clones (C10-20 derived from CIP701165 and E86-69 derived from CIP703767) with good growth vigor and fruit-setting rate were chosen for genetic analyses and continual selfing. To evaluate the genome homozygosity and mutation burden, 153 diploid potatoes were used, including two $BC_1$ clones (C10-20 and E86-69) and 151 accessions that have been reported in a previous study (Zhang et al., 2019).

Results

In nature, nearly all diploid potatoes are self-incompatible, which is controlled by the highly polymorphic S-RNase alleles (Takayama and Isogai, 2005). To develop inbred lines from heterozygous diploid clones, it is necessary to break self-incompatibility. In this study, four diploid clones belonging to different subgroups were used to create inbred lines. PG6359 and RH are two natural self-compatible accessions, which have previously been reported (Clot et al., 2020; Peterson et al., 2016; Zhang et al., 2019). The self-compatibility in PG6359 was conferred by a low-expressed S-RNase allele, $S_{S11}$ (Zhang et al., 2019). For the other two clones, CIP701165 and CIP703767, they were self-incompatible, which was overcome by introgression of the Sli gene from a breeding line E172. Two BC1 clones, C10-20 and E86-69, derived from CIP701165 and CIP703767, respectively, were selected to develop inbred lines. Development of these inbred lines, carrying different self-compatibility genes, could avoid the detrimental effects of any deleterious mutations, linked with either self-compatibility gene, being exposed in the $F_1$ hybrids.

Figure 2:
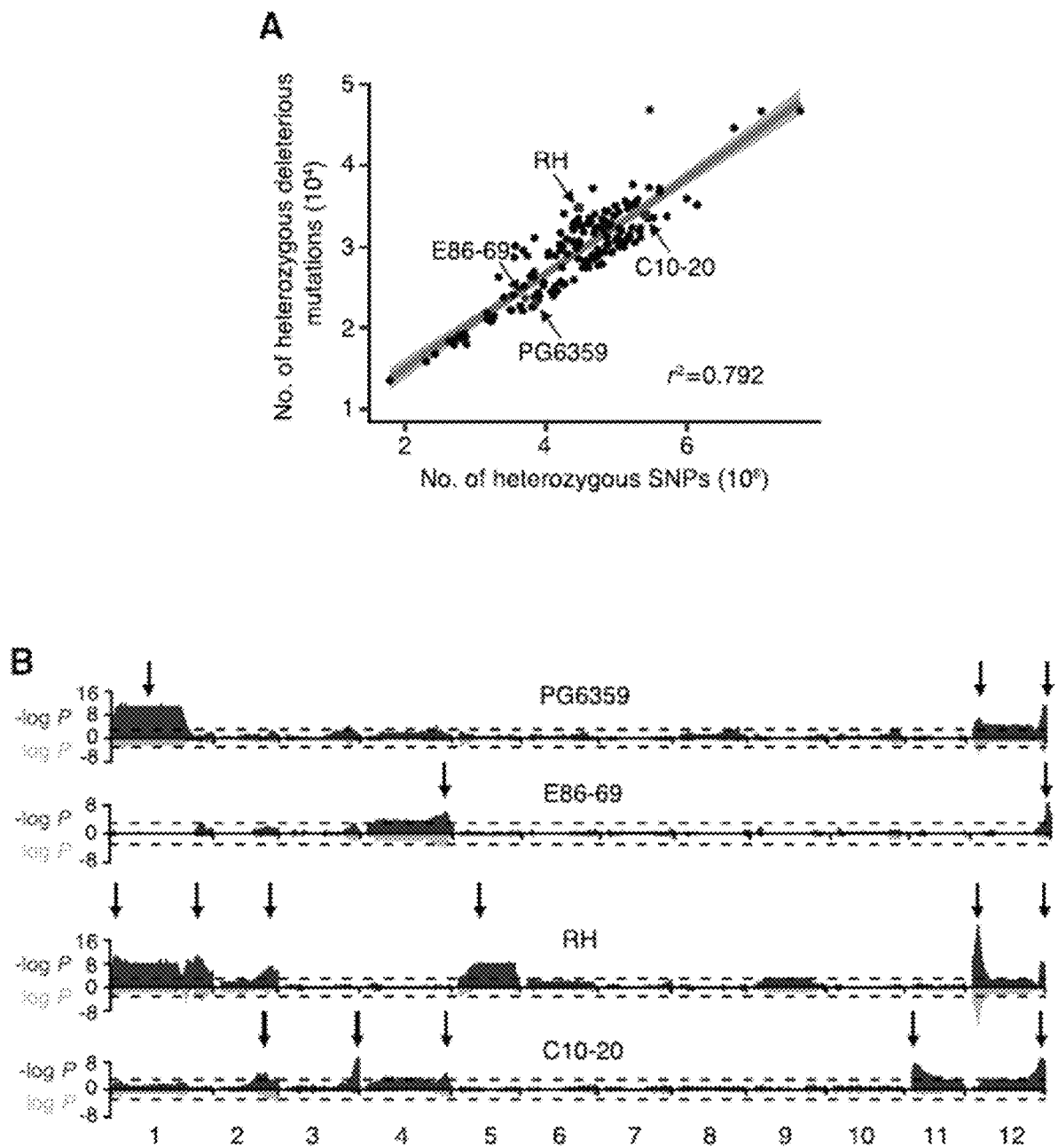
FIG. 2 illustrates the selection of the starting materials. (A) The correlation between number of heterozygous SNPs and heterozygous deleterious mutations. Arrows represent the four clones used in this study. Light grey shaded region indicates 95% confidence interval. (B) Segregation distortions (SDs) of bins in four $S_1$ populations; for each population, 112 $S_1$ plants were used for genetic analysis. The y-axis represents the $-\log P$ and $\log P$ for the $\chi 2$ value of each bin, at the zygotic (dark grey region above the x-axis) and gametic (light grey region below the x-x-axis) stages, respectively. Arrows indicated the SD regions.

Another crucial feature of the starting material is the number of deleterious mutations. Such deleterious substitutions were predicted based on amino acid conservation, using the SIFT algorithm (Vaser et al., 2016). The genomes of 153 diploid clones were analyzed and it was found that genomic heterozygosity is positively correlated with the number of deleterious mutations (FIG. 2, panel A). Among the four clones used in this study, PG6359 and E86-69 harbor relatively less mutations. Genomic analysis revealed that PG6359 contains several large homozygous segments (Zhang et al., 2019), covering 12.17% of the entire genome. Since this clone is self-compatible, it was inferred that some large-effect deleterious mutations had been purged, either during selfing or inbreeding. Likewise, due to backcrossing, some genomic regions in E86-69 were already homozygous, covering 35.47% of the entire genome.

However, RH and C10-20 failed to produce inbred lines. These two clones contain relatively more deleterious mutations (FIG. 2, panel A), and their progeny became very weak and seldom flowered after two generations of selfing. Analysis of a small $S_1$ population from each clone showed that the SDs in RH and C10-20 are more than that in PG6359 and E86-69 (FIG. 2, panel B), which increases the difficulty in developing pure inbred lines.

Taken together, this example demonstrates successful selection of starting material for developing highly homozygous inbred lines. Importantly, the starting material, with lower heterozygosity and less deleterious mutations, offers a greater potential for development into inbred lines.

Example 2: Genetic Analyses of $S_1$ Population and Identification of Large-Effect Deleterious Mutations This example illustrates the second step of hybrid diploid potato breeding by genome design: analyzing the $S_1$ population of the starting material to identify segregation distortion regions (SDs) and genetic loci carrying large-effect deleterious mutations or controlling agronomic traits. Specifically, this example uses the diploid clone PG6359 to illustrate how to develop homozygous inbred lines from a heterozygous diploid clone.

Methods and Materials

Genome Resequencing and Calculation of Genome Homozygosity

Total DNA was isolated from fresh leaves and subjected to genome re-sequencing, using the Illumina HiSeq X Ten or NovoSeq platforms. The insert size of the libraries was 250-300 bp, and the read length was 150 bp. For parental clones, PG6359, RH, C10-20 and E86-69, -20 Gb clean data were generated, and for each selected progeny, ~2 Gb clean data were generated. Short reads were aligned against the potato reference genome DM1-3 516 R44 (DM) (V4.03) (PGSC, 2011; Sharma et al., 2013) using BWA (Li et al., 2013), and SNPs were extracted using Samtools (Li et al., 2009) and BCFtools. Deduction of two haplotypes of the parental clone, construction of bin maps, and analysis of segregation distortions were performed, according to a previous study (Zhang et al., 2019). The genome homozygosity of selfed progenies was calculated using the following formula:

$$Homozygosity = \frac{Length\ of\ homozygous\ bins}{Potato\ genome\ size} \times 100\%$$

Phenotyping Assay

All potato materials used in this study were grown under greenhouse conditions. To evaluate the phenotype of the $S_1$ population of PG6359, three clones for each genotype were transplanted in the greenhouse. At the flowering stage, floral bud abortion was observed by eye. When the tubers were harvested, tuber shape was visually scored as '1' (round), '0' (long), or '-' (not sure), and tuber flesh color was visually scored as '1' (yellow), '0' (white), or '-' (not sure). For these three qualitative traits, the corresponding genetic loci were mapped by bulked segregant analyses (Takagi et al., 2013). Tuber number refers to the sum of tubers with diameter of transection ≥20 mm collected from three replicates. Tuber weight of four $F_1$ hybrids and their parents refers to the average tuber weight per plant with diameter of transection ≥10 mm.

Cloning the FBA1 Gene

To fine map the FBA1 gene, the heterozygous Insertions/Deletions (InDels) in PG6359, with index 0.3-0.7 and length 2-50 bp, were extracted, using Platypus (V0.7.4) (Manary et al., 2014). The 150-bp flanking sequences of InDels were extracted and used to design polymorphic markers. More than 5000 $S_1$ individuals of PG6359 were used to narrow down the candidate region of FBA1. Total RNA from the anthers of young floral buds was extracted, using an RNA-prep Pure Plant Kit (TIANGEN, China). About 1 g of total RNA was used for First-strand cDNA synthesis (Prime-Script™ RT reagent Kit with gDNA Eraser, TaKaRa, Japan, Cat #RR047A). RT-qPCR was conducted by using the ABI StepOne-Plus System and TB Green Premix Ex Taq™ (TaKaRa, Japan), following the manufacturer's instructions. Relative expression of the candidate genes was calculated using the 2-ΔΔCt method. To knock out the candidate gene, the single guide RNA was designed and incorporated into the CRISPR/Cas9 vector, pKSE401, using BsaI (NEB, USA, Cat #R3535) and T4 DNA Ligase (NEB, USA, Cat #M0202S) (Xing et al., 2014). The *agrobacterium*-mediated method was used to transform the stem nodes of potato (Ye et al., 2018).

Carotenoid Analysis

Carotenoid analysis, including lutein, zeaxanthin and β-carotene, was performed according to that described by Huang et al. (2018). Briefly, 200 mg lyophilized tuber was extracted with acetone until they were almost colorless. The extracts were filtered through a 0.22 m Millipore organic membrane and then were analyzed by an Agilent Ultra High Performance Liquid Chromatography (UHPLC) 1290 Infinity. To separate lutein and zeaxanthin, a liquid chromatography method was developed in which UHPLC was equipped with a Waters YMC Carotenoid C30 column (5 m, 4.6×250 mm), and the mobile phase consisted of solvent A (methanol) and solvent B (methyl tertiary butyl ether). At a flow rate of 1.0 mL·min−1, 10 μL of each sample was analyzed in a gradient mode (0-45 min: linear gradient of 0-15% of B; 40-45 min: linear gradient of 15-60% of B; 55-60 min: linear gradient of 60-70% of B; 60-62 min: linear gradient of 70-0% of B). Compounds were detected at 480, 450, and 280 nm, and the retention times, absorption spectra, and peak area of each pigment were compared with authentic compounds.

Prediction of Deleterious Substitutions

To predict the deleterious substitutions of 153 diploid accessions, ~10×genome sequences of each clone were used to extract SNPs. The index of heterozygous SNPs was ≥0.3 and ≤0.7, and that of homozygous SNPs was ≥0.9 or ≤0.1. Amino acid substitutions and their effects on protein function were predicted with the SIFT algorithm (Vaser et al., 2016). An amino acid substitution was predicted to be deleterious if the score was ≤0.05 and tolerated if the score was >0.05. To predict the deleterious substitutions in two inbred lines, A6-26 and E4-63, the assembled contigs were aligned to the DM genome (V4.03) and used to call SNPs.

Results

A total of 825 $S_1$ individuals of PG6359 were sequenced, among which 256 plants could set fruit after artificial self-pollination. The genome-wide SDs were then analyzed at the seedling and fruit-setting stages. The SDs on chromosome 1 (Chr. 1), Chr. 3 and Chr. 12 were found to be the same at both developmental stages, indicating that these SDs are associated to the early-stage characters, such as gametic or zygotic survival, growth vigor, etc. In a previous study, the self-compatibility gene, $S_{S11}$, and the leaf chlorosis gene, yl1, were mapped on Chr. 1 and Chr. 12, respectively (Zhang et al., 2019). At the fruit-setting stage, an additional SD was detected on Chr. 2, implicating it as being related to fertility, or other late-stage traits.

Figure 3:
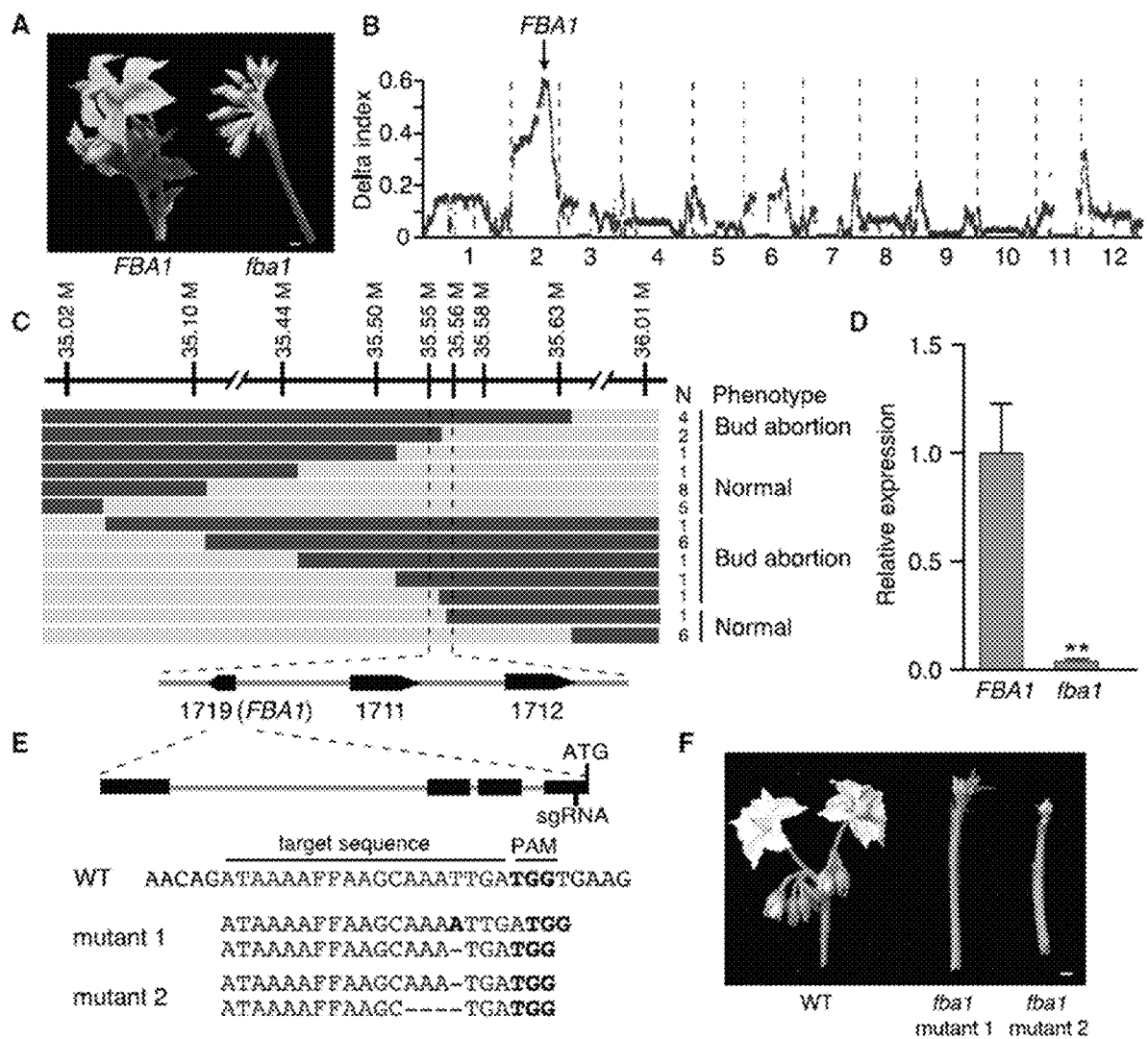
FIG. 3 illustrates the identification of a large-effect deleterious mutation controlling male fertility. (A) The phenotype of plants with normal flowers (FBA1) and floral bud abortion (fba1). Scale bar represents 0.5 cm. (B) Bulked segregant analysis located the FBA1 gene on Chr. 2. (C)

Due to the reliance on asexual propagation in potato, some genes controlling fertility were negatively selected (Hardigan et al., 2017), an important point for consideration, as fertility is a crucial factor to the development of inbred lines. In addition, because of inbreeding depression, some selfed progeny showed very weak fertility or male sterility. Understanding these deleterious mutations affecting fertility is essential for developing inbred lines. In the progeny of PG6359, the floral buds of some plants aborted before flowering; this trait was designated as floral bud abortion 1 (fba1) (FIG. 3, panel A). Very few flowers on these plants blossomed, but for these, their pollen was sterile.

Bulked segregant analysis revealed that fba1 was controlled by a single locus on Chr. 2, which co-localized with the SD on Chr. 2 (FIG. 3, panel B). Further studies mapped fba1 to a 11 kb interval containing three annotated genes (FIG. 3, panel C). Among them, PGSC0003DMG400021719, encoding a bHLH transcription factor, was specifically expressed in the stamen and its expression was depressed in mutant plants (FIG. 3, panel D). The Arabidopsis orthologous gene, DYT1, is required for anther development (Cui et al., 2016). Knockout of StDYT1 in potato resulted in the same phenotype as fba1 (FIG. 3, panel E and FIG. 3, panel F), which confirmed that StDYT1 regulates stamen development in potato and its mutation represents a major deleterious allele affecting fertility.

The selfed progeny of PG6359 also showed diverse variations in tuber-related traits, with tuber size and tuber number per plant showing a continuous distribution, indicating these traits are controlled by multiple loci. In contrast, tuber shape and flesh color exhibited characteristics of qualitative traits. Bulked segregant analysis located the locus controlling round tuber shape to Chr. 10, corresponding to the Ro gene (Bonierbale et al., 1988; van Eck et al., 1994). As long and round tuber shapes have different commercial values, and no SD colocalizes with this trait, both haplotypes were kept in our breeding project. The locus controlling flesh color was mapped to Chr. 3, corresponding to the Y gene (Kloosterman et al., 2010). The yellow flesh allele, Y, located on haplotype B, controls carotenoid accumulation, a nutritional trait. In addition, the haplotype A, carrying the white flesh allele, y, showed distorted segregation, indicating that it is linked with a large-effect deleterious mutation. Thus, the haplotype A needs to be purged during the development of inbred lines.

Taken together, this example demonstrates successful analysis of the $S_1$ population of the starting material to identify segregation distortion regions (SDs) and genetic loci carrying large-effect deleterious mutations or controlling agronomic traits.

Example 3: Breaking the Close Linkage of Two Deleterious Mutations in Repulsion Phases Based on the genetic analyses in Example 2, a pipeline was designed to eliminate deleterious or undesirable alleles as well as stack beneficial alleles. First, selected $S_1$ individuals carrying four beneficial alleles ($S_{S11}$ for self-compatibility, YL1 for normal leaves, FBA1 for fertility, and Y for yellow flesh) were selected to be selfed. Next, the performance and homozygosity of the resultant $S_2$ plants were assessed to select individuals with relatively high homozygosity and desired traits for seed collection. Finally, using the same selection criteria, the resultant population was further self-pollinated, for 2-4 times, to ultimately obtain inbred lines with high homozygosity.

The average genome homozygosity of $S_1$ plants was 48.32%, varying from 19.30% to 74.76%. A total of 86 $S_1$ individuals containing the above four traits were selected to develop inbred lines. About 9,000 $S_2$ plants were transplanted into the greenhouse, and at the seedling stage, all plants with leaf chlorosis or weak growth vigor were removed. The remaining plants were manually self-pollinated. According to growth vigor, fruit setting and tuber-related traits, 116 $S_2$ individuals were selected and re-sequenced. Unexpectedly, a peak of heterozygous regions was observed at the end of Chr. 12 (ST4.03ch12: 60,229,075-61,165,650) (FIG. 4, panel A). Among the selected 116 $S_2$ plants, 107 were heterozygous at this locus. As haplotype B carries the deleterious allele, yl1, its homozygotes were discarded at the seedling stage. But the homozygous haplotype A was also seldom selected, so this locus was re-analyzed using the $S_1$ population. It was then found that the homozygous haplotype A showed significantly distorted segregation, the ratio of which is only 1.98%, far below a quarter (FIG. 4, panel B). This indicates haplotype A contains a large-effect deleterious mutation, affecting the survival of homozygotes, designated as large-effect deleterious mutation 1 (led1). To develop inbred lines, it is necessary to break the tight linkage between these two deleterious mutations in repulsion phases.

Due to the relatively high recombination rate at the end of Chr. 12, four $S_1$ recombinants were identified in this region. The leaf color of the recombinant R1 was green, and its $S_2$ progeny showed segregation in their leaf color, indicating that the yl1 gene was located downstream of bin128 (FIG. 4, panel C). Leaf color of the recombinant R2 and its $S_2$ progeny was green, and its $S_2$ progeny showed distorted segregation in bin124, suggesting that the other deleterious mutation, led1, was located upstream of bin125 (FIG. 4, panel D). According to the genotype and phenotype of these two $S_1$ recombinants, and their $S_2$ progeny, it was concluded that the close linkage between two deleterious mutations was broken. In the $S_2$ population, nine individuals carrying the beneficial alleles, LED1 and YL1, were obtained in the coupling phase (FIG. 4, panel E), all of which were derived from the R2 recombinant.

Taken together, this example demonstrates successful breaking of the close linkage of two deleterious mutations in repulsion phases. Importantly, with phenotype-based selection, it is sometimes impossible to identify and purge the closely linked deleterious mutations in the repulsion phases. In this case, genomic analysis and selection was essential.

Example 4: Development of Highly Homozygous Inbred Lines by Genome-Assisted Selection This example illustrates the development of highly homozygous inbred lines, by continuous selfing and genome-assisted selection, to purge deleterious mutations and stack beneficial alleles.

Although the average homozygosity of $S_2$ plants increased to 72.76% (FIG. 5, panel A), the number of heterozygous regions had not decreased (P=0.81) (FIG. 5, panel B). It was further found that the number of crossovers in the $S_2$ progeny increased by 50.21% (P=1.40×10-33) (FIG. 5, panel C), indicating that new crossovers occurred within heterozygous regions. For example, in a heterozygous region on Chr. 1, eleven crossovers were detected in nine $S_2$ individuals from the same family. To accelerate the purification of inbred lines, those $S_2$ plants with genome homozygosity <70% were eliminated, and seeds of the remaining 79 plants were sown. Finally, 44 $S_3$ families (~8,000 plants) with high germination rate were transplanted for further study.

According to the same selection process, this population continued to be selfed for a further two generations. Finally, multiple highly homozygous inbred lines were obtained carrying the beneficial alleles (FIG. 5, panel D). The average homozygosity of $S_5$ plants was raised to 97.54% (91.79%~99.94%) (FIG. 5, panel A). With an increase in homozygosity, in advanced inbred lines, the number and length of the heterozygous regions in each generation consistently underwent a decrease. In the $S_5$ generation, more than 95% of the heterozygous regions were shorter than 10 Mb.

Taken together, this example demonstrates successful development of highly homozygous inbred lines by genome-assisted selection.

Example 5: Generation of Vigorous $F_1$ Hybrids

This example illustrates the process of crossing inbred lines derived from different lineages to obtain $F_1$ hybrids and evaluate them for performance.

Employing the same pipeline as described in the preceding examples, inbred lines were also developed using a vigorous and self-compatible clone, E86-69. Among 500 $S_1$ plants of E86-69, 262 individuals bearing fruit, by selfing, were re-sequenced and used to construct the bin map. Only two regions with strong SD were identified ($\chi 2$ test, P<1E-10). The number of SDs is crucial for developing inbred lines; lower SDs facilitate development of inbred lines. No visible phenotypic defect was linked with the SD on Chr. 04 and hence we only selected the beneficial haplotype, at this locus, and did not perform further analyses. In another study, it was confirmed that the SD on Chr. 12 was caused by the self-compatibility gene, Sli (Ma et al., 2021). Only the pollen carrying the Sli gene could penetrate the style and complete the double fertilization, whereas growth of pollen tubes without Sli was inhibited, which caused the observed segregation distortion. According to this mechanism, all selfed progeny were self-compatible. Thus, it was unnecessary to make selections at this locus.

The average homozygosity of $S_1$ plants was 63.85%, varying from 43.16% to 81.25%. The seeds from 44 $S_1$ plants, with homozygosity >70%, were germinated for developing inbred lines. After another two generations of selfing, the average homozygosity was increased to 91.85% and 23 $S_3$ plants had homozygosity higher than 95%. Different from the PG6359 population, the number of heterozygous regions in the E86-69 population consistently decreased along with the continuous increase of crossovers.

With the availability of two sets of inbred lines derived from different lineages, crosses were made between them. As expected, the performance of $F_1$ hybrids between homozygous inbred lines was very uniform, whereas those derived from heterozygous parental lines showed a great segregation in tuber traits. Moreover, the inbred-line-based $F_1$ hybrids had strong heterosis in growth vigor and yield in the greenhouse (FIG. 6, panel A and FIG. 6, panel B). Compared with parental lines, the yield of these $F_1$ hybrids was increased by at least 31% (FIG. 6, panel C). For the combination A6-10×E4-64, the $F_1$ hybrid yield was 3.38 times that of the mid-parent value.

The mini-tubers, harvested from true-seed plants, were grown in the field, in Dehong (24° 43'N and 98° 58'E), Yunnan Province, to test the yield potential of these $F_1$ hybrids. Due to severe inbreeding depression, the resultant inbred lines performed very weakly in the field, and only a few tubers could be harvested. In contrast, the $F_1$ plants grew well under these field conditions, and the average yield was twice that obtained in the greenhouse (FIG. 6, panel D). Furthermore, these $F_1$ tubers were rich in carotenoids (59.63~72.06 mg·kg-1 fry weight) and dry matter (23.10%~26.02%) (FIG. 6, panel E). Unexpectedly, due to the self-compatibility and recovered fertility, the $F_1$ hybrids produced abundant fruits (FIG. 6, panel D), which competed with the underground tubers for nutrients.

Taken together, this example demonstrates generation of vigorous $F_1$ hybrids.

Example 6: Genome Complementarity of Two Inbred Lines

This example illustrates genome complementarity of inbred lines as an underlying mechanism for the highly vigorous $F_1$ potato hybrids of the present disclosure.

Methods and Materials

HiFi Library Preparation, Sequencing, and Genome Assembly

Genomic DNA was extracted from in vitro-propagated seedlings. Each SMRTbell library was constructed using the Pacific Biosciences SMRTbell template prep kit 1.0. The constructed libraries were size-selected on a BluePippin™ system, followed by primer annealing and the binding of SMRT bell templates to polymerases with the DNA/Polymerase Binding Kit.

Sequencing was carried out on the Pacific Bioscience Sequel II platform at Annoroad Gene Technology company (Beijing, China). HiFi reads were generated, using the PacBio tools package, pbccs, with default parameters. HiFi reads were assembled by Flye V2.7.1 (-pacbio-hifi-keep-haplotypes) (Kolmogorov et al., 2019). Hi-C data were aligned to the assemblies by Juicer software (Durand et al., 2016), while super-scaffolds were anchored by 3d-dna pipeline (Dudchenko et al., 2017).

Genome Annotation

RepeatMasker was used to mask the repeat sequences. The pipeline for annotation included ab initio prediction, homolog prediction and transcripts annotation. GeneMark (Bruna et al., 2020), SNAP (Korf, 2004) and AUGUSTUS V3.3 (Stanke et al., 2004) were used for ab initio prediction. Exonerate was used for homolog prediction. RNA-seq were aligned to the assemblies, using HISAT2 V2.1.0 (Pertea et al., 2016), and expression levels were quantified, using StringTie V1.3.6 (Pertea et al., 2015). Transcripts were assembled by Trinity and used as training model for the PASA pipeline (Grabherr et al., 2011; Haas et al., 2003). Finally, all predicted evidence was integrated, by EVidenceModeler V1.1.1 (Haas et al., 2008), to generate the final annotation gene set.

Variants Calling

Variants, including SNPs, insertions, deletions, and structural variations of the two assemblies and DM reference genome (V4.03) were carried out by the smartie-sv pipeline (Kronenberg et al., 2018). Alignments were launched by a modified version of BLASR (Chaisson and Tesler, 2012), which was designed to align large divergent contigs against a reference genome.

Gene Comparative Analysis and Specific Expression

The core and specific gene sets of the two de novo assemblies and DM reference genome (V4.03) were estimated based on OrthoFinder V2.3.3 (Emms and Kelly, 2015) (-S mmseqs-T raxml-M msa) gene family clustering results. Unassigned genes were defined as the specific genes for each accession.

Results

To preliminarily explore the genetic basis of heterosis in $F_1$ hybrids, the genomes were de novo assembled for the two parents of the $F_1$ hybrid H1, A6-26 (homozygosity=98.16%) and E4-63 (homozygosity=98.52%) using Pacbio HiFi reads. The assembled genome sizes of A6-26 and E4-63 were 748 Mb (contig N50=2.64 Mb) and 740 Mb (contig N50=3.89 Mb), respectively. More than 98% of the sequences of these two genomes were categorized and anchored to 12 super-scaffolds, representing 12 pseudo-chromosomes, and some 97% of embryophyta BUSCO genes could be aligned to each assembly. The average alignment rate of transcriptome data from A6-26 and E4-63 was 97.46% and 97.75%, respectively. These data demonstrated the high continuity and completeness of these two genomes. 37,948 and 37,214 high-confidence protein-coding genes were annotated for A6-26 and E4-63, respectively.

Comparisons with the potato reference genome DM1-3 516 R44 (hereafter referred as DM) revealed 12,023 specifically identified genes in these two inbred lines. As DM is male-sterile and has defects in tuber development, these two inbred lines could be used as reference genomes to study fertility and tuber development of potato, as well as other important biological processes.

In addition, the genetic variants were also compared between DM and these two inbred lines. For each assembly, some three million variants were identified (Table 1).

TABLE 1

Genetic variants between the potato DM genome and two inbred lines.

| Variants | A6-26 vs DM[a] | E4-63 vs DM | Overlapped between A6-26 and E4-63 |
|---|---|---|---|
| SNPs | 2,184,072 | 2,255,668 | 459,515 (11.55%) |
| InDels (<50 bp) | 678,669 | 731,456 | 143,7123 (11.35%) |
| Structural variations (≥50 bp) | 62,720 | 66,293 | 18,660 (16.91%) |

[a]The genome version 4.03 was used for comparative analysis.

The overlapped SNP, InDels and structural variations between A6-26 and E4-63 were 11.55%, 11.35% and 16.91%, respectively, indicating that nearly 90% variants should be heterozygous in their $F_1$ hybrid. 10,994 and 11,093 deleterious substitutions were further predicted in A6-26 and E4-63, respectively, but only 8.36% were overlapped, suggesting that the detrimental effects of most deleterious substitutions will be masked in $F_1$ hybrid. These deleterious substitutions involve 7,414 genes, among which 2,217 genes showed differential expression in the tubers of A6-26 and E4-63. The genomic complementarity of two inbred lines, to some extent, may explain the heterosis of the $F_1$ hybrid.

Taken together, this example demonstrates genome complementarity of inbred lines could be a possible underlying mechanism for the highly vigorous $F_1$ potato hybrids described in the present disclosure.

The following list provides references cited herein, each of which is incorporated by reference in its entirety.

REFERENCES

Bethke, P. C., Nassar, A. M. K., Kubow, S., Leclerc, Y. N., Li, X., Haroon, M., Molen, T., Bamberg, J. B., Martin, M., and Donnelly, D. J. (2014). History and origin of Russet Burbank (Netted Gem) a sport of Burbank. *Am. J. Potato Res.* 91, 594-609.

Bonierbale, M. W., Plaisted, R. L., and Tanksley, S. D. (1988). RFLP maps based on a common set of clones reveal modes of chromosomal evolution in potato and tomato. *Genetics* 120, 1095-1103.

Bruna, T., Lomsadze, A., Borodovsky, M. (2020). GeneMark-EP+: eukaryotic gene prediction with self-training in the space of genes and proteins. *NAR Genom. Bioinform.* 2, lqaa026.

Chaisson, M. J., and Tesler, G. (2012). Mapping single molecule sequencing reads using basic local alignment with successive refinement (BLASR): application and theory. *BMC Bioinformatics* 13, 238.

Charlesworth, D., and Willis, J. H. (2009). The genetics of inbreeding depression. *Nat. Rev. Genet.* 10, 783-796.

Clot, C. R., Polzer, C., Prodhomme, C., Schuit, C., Engelen, C. J. M., Hutten, R. C. B., and van Eck, H. J. (2020). The origin and widespread occurrence of Sli-based self-compatibility in potato. *Theor. Appl. Genet.* 133, 2713-2728.

Cui, J., You, C., Zhu, E., Huang, Q., Ma, H., and Chang, F. (2016). Feedback regulation of DYT1 by interactions with downstream bHLH factors promotes DYT1 nuclear localization and anther development. *Plant Cell* 28, 1078-1093.

Dudchenko, O., Batra, S. S., Omer, A. D., Nyquist, S. K., Hoeger, M., Durand, N. C., Shamim, M. S., Machol, I., Lander, E. S., Aiden, A. P., et al. (2017). De novo assembly of the *Aedes aegypti* genome using Hi-C yields chromosome-length scaffolds. *Science* 356, 92-95.

Duncan et al., The production of callus capable of plant regeneration from immature embyros of numerous *Zea mays* genotypes, *Planta,* 165, 322-332 (1985).

Durand, N. C., Shamim, M. S., Machol, I., Rao, S. S., Huntley, M. H., Lander, E. S., and Aiden, E. L. (2016). Juicer provides a one-click system for analyzing Loop-resolution Hi-C experiments. *Cell Syst.* 3, 95-98.

Emms, D. M., and Kelly, S. (2015). OrthoFinder: solving fundamental biases in whole genome comparisons dramatically improves orthogroup inference accuracy. *Genome Biol.* 16, 157.

Enciso-Rodriguez, F., Manrique-Carpintero, N. C., Nadakuduti, S. S., Buell, C. R., Zarka, D., and Douches, D. (2019). Overcoming self-incompatibility in diploid potato using CRISPR-Cas9. Front. *Plant Sci.* 10, 376.

Grabherr, M. G., Haas, B. J., Yassour, M., Levin, J. Z., Thompson, D. A., Amit, I., Adiconis, X., Fan, L., Raychowdhury, R., Zeng, Q., et al. (2011). Full-length transcriptome assembly from RNA-Seq data without a reference genome. *Nat. Biotechnol.* 29, 644-652.

Haas, B. J., Delcher, A. L., Mount, S. M., Wortman, J. R., Smith, R. K., Jr., Hannick, L. I., Maiti, R., Ronning, C. M., Rusch, D. B., Town, C. D., et al. (2003). Improving the *Arabidopsis* genome annotation using maximal transcript alignment assemblies. *Nucleic Acids Res.* 31, 5654-5666.

Haas, B. J., Salzberg, S. L., Zhu, W., Pertea, M., Allen, J. E., Orvis, J., White, O., Buell, C. R., and Wortman, J. R. (2008). Automated eukaryotic gene structure annotation using EVidenceModeler and the Program to Assemble Spliced Alignments. *Genome Biol.* 9, R7.

Hardigan, M. A., Laimbeer, F. P. E., Newton, L., Crisovan, E., Hamilton, J. P., Vaillancourt, B., Wiegert-Rininger, K., Wood, J. C., Douches, D. S., Farre, E. M., et al. (2017). Genome diversity of tuber-bearing *Solanum* uncovers complex evolutionary history and targets of domestication in the cultivated potato. *Proc. Natl. Acad. Sci.* USA 114, E9999-E10008.

Hosaka, K., and Hanneman Jr., R. E. (1998). Genetics of self-compatibility in a self-incompatible wild diploid potato species *Solanum chacoense*. 2. Localization of an S-locus inhibitor (Sli) gene on the potato genome using DNA markers. *Euphytica* 103, 265-271.

Huang, W., Lin, Y., He, M., Gong, Y., and Huang, J. (2018). Induced High-Yield Production of zeaxanthin, lutein, and beta-carotene by a mutant of *chlorella* zofingiensis. *J. Agric. Food. Chem.* 66, 891-897.

Jansky, S. H., Charkowski, A. O., Douches, D. S., Gusmini, G., Richael, C., Bethke, P. C., Spooner, D. M., Novy, R. G., De Jong, H., De Jong, W. S., et al. (2016). Reinventing potato as a diploid inbred line-based crop. *Crop Sci.* 56, 1412-1422.

Kamo et al., "Regeneration of *Zea mays* L. From Embryogenic Callus", *Bot. Gaz.,* 146, 327-334 (1985).

Kloosterman, B., Oortwijn, M., uitdeWilligen, J., America, T., de Vos, R., Visser, R. G. F., and Bachem, C. W. B. (2010). From QTL to candidate gene: Genetical genomics of simple and complex traits in potato using a pooling strategy. *BMC Genomics* 11, 158.

Kolmogorov, M., Yuan, J., Lin, Y., and Pevzner, P. A. (2019). Assembly of long, error-prone reads using repeat graphs. *Nat. Biotechnol.* 37, 540-546.

Korf, I. (2004). Korf, I. Gene finding in novel genomes. *BMC Bioinformatics* 5, 59. *BMC bioinformatics* 5, 59.

Kronenberg, Z. N., Fiddes, I. T., Gordon, D., Murali, S., Cantsilieris, S., Meyerson, O. S., Underwood, J. G., Nelson, B. J., Chaisson, M. J. P., Dougherty, M. L., et al. (2018). High-resolution comparative analysis of great ape genomes. *Science* 360, eaar6343.

Li, H. (2013) Aligning sequence reads, clone sequences and assembly contigs with BWA-MEM. *arXiv,* 1303.3997

Li, H., Handsaker, B., Wysoker, A., Fennell, T., Ruan, J., Homer, N., Marth, G., Abecasis, G., Durbin, R. (2009) The Sequence Alignment/Map (SAM) Format and SAMtools. *Bioinformatics* 25, 1653-1654.

Li, Y., Li, G., Li, C., Qu, D., and Huang, S. (2013). Prospects of diploid hybrid breeding in potato. *Chinese Potato* 27, 96-99.

Lindhout, P., Meijer, D., Schotte, T., Hutten, R. C. B., Visser, R. G. F., and van Eck, H. J. (2011). Towards $F_1$ hybrid seed potato breeding. *Potato Res.* 54, 301-312.

Manary, M., Singhakul, S., Flannery, E., Bopp, S., Corey, V., Bright, A., McNamara, C., Walker, J., and Winzeler, E. (2014). Identification of pathogen genomic variants through an integrated pipeline. *BMC Bioinformatics* 15, 63.

Manrique-Carpintero et al. Comparative analysis of regions with distorted segregation in three diploid populations of potato. *G3: Genes, Genomes, Genetics* 6.8 (2016): 2617-2628.

Miki et al., In: Methods in Plant Molecular Biology and Biotechnology, Glick and Thompson (Eds.), CRC Press, Inc., Boca Raton, 1993.

Pertea, M., Kim, D., Pertea, G. M., Leek, J. T., and Salzberg, S. L. (2016). Transcript-level expression analysis of RNA-seq experiments with HISAT, StringTie and Ballgown. *Nat. Protoc.* 11, 1650-1667.

Pertea, M., Pertea, G. M., Antonescu, C. M., Chang, T. C., Mendell, J. T., and Salzberg, S. L. (2015). StringTie enables improved reconstruction of a transcriptome from RNA-seq reads. *Nat. Biotechnol.* 33, 290-295.

Peterson, B. A., Holt, S. H., Laimbeer, F. P. E., Doulis, A. G., Coombs, J. J., Douches, D. S., Hardigan, M. A., Buell, C. R., and Veilleux, R. E. (2016). Self-fertility in a cultivated diploid potato population examined with the Infinium 8303 potato single-nucleotide polymorphism array. *Plant Genome* 9, 1-13.

PGSC (2011). Genome sequence and analysis of the tuber crop potato. *Nature* 475, 189-195.

Sharma, S. K., Bolser, D., de Boer, J., Sonderkaer, M., Amoros, W., Carboni, M. F., D'Ambrosio, J. M., de la Cruz, G., Genova, A. D., Douches, D. S., et al. (2013). Construction of reference chromosome-scale pseudomolecules for potato: integrating the potato genome with genetic and physical maps. *G3: Genes, Genomes, Genetics* 3, 2031-2047.

Spooner, D. M., Ghislain, M., Simon, R., Jansky, S. H., and Gavrilenko, T. (2014). Systematics, diversity, genetics, and evolution of wild and cultivated potatoes. *Bot. Rev.* 80, 283-383.

Stanke, M., Steinkamp, R., Waack, S., and Morgenstern, B. (2004). AUGUSTUS: a web server for gene finding in eukaryotes. *Nucleic Acids Res.* 32, W309-312.

Stokstad, E. (2019). The new potato. *Science* 363, 574-577.

Takagi, H., Abe, A., Yoshida, K., Kosugi, S., Natsume, S., Mitsuoka, C., Uemura, A., Utsushi, H., Tamiru, M., Takuno, S., et al. (2013). QTL-seq: rapid mapping of quantitative trait loci in rice by whole genome resequencing of DNA from two bulked populations. *Plant J.* 74, 174-183.

Takayama, S., and Isogai, A. (2005). Self-incompatibility in plants. Annu. Rev. *Plant Biol.* 56, 467-489.

van Eck, H. J., Jacobs, J. M. E., Stam, P., Ton, J., Stiekema, W. J., and Jacobsen, E. (1994). Multiple alleles for tuber shape in diploid potato detected by qualitative and quantitative genetic analysis using RFLPs. *Genetics* 137, 303-309.

van Lieshout, N., van der Burgt, A., de Vries, M. E., Ter Maat, M., Eickholt, D., Esselink, D., van Kaauwen, M. P. W., Kodde, L. P., Visser, R. G. F., Lindhout, P., et al. (2020). Solyntus, the new highly contiguous reference genome for potato (*Solanum tuberosum*). *G3: Genes, Genomes, Genetics* 10, 3489-3495.

Vaser, R., Adusumalli, S., Leng, S. N., Sikic, M., and Ng, P. C. (2016). SIFT missense predictions for genomes. *Nat. Protoc.* 11, 1-9.

West et al., "Embryogenesis in Higher Plants: An Overview", *The Plant Cell,* 5, 1361-1369 (1993).

Xing, H., Dong, L., Wang, Z., Zhang, H., Han, C., Liu, B., Wang, X., and Chen, Q. (2014). A CRISPR/Cas9 toolkit for multiplex genome editing in plants. *BMC Plant Biol.* 14, 327.

Ye, M., Peng, Z., Tang, D., Yang, Z., Li, D., Xu, Y., Zhang, C., and Huang, S. (2018). Generation of self-compatible diploid potato by knockout of S-RNase. *Nat. Plants* 4, 651-654.

Zhang, C., Wang, P., Tang, D., Yang, Z., Lu, F., Qi, J., Tawari, N. R., Shang, Y., Li, C., and Huang, S. (2019). The genetic basis of inbreeding depression in potato. *Nat. Genet.* 51, 374-378.

Zhang, C., Yang, Z., Tang, D., Zhu, Y., Wang, P., Li, D., Zhu, G., Xiong, X., Shang, Y., Li, C., and Huang, S. (2021). Genome design of hybrid potato. *Cell,* 184(15), 3873-3883.

DEPOSIT INFORMATION

Potato Inbred Line "A6-10"

A deposit of the potato inbred line "A6-10" is maintained by the Agricultural Genomics Institute at Shenzhen, Chinese Academy of Agricultural Sciences, Shenzhen, Guangdong 518120, China. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the China Center for Type Culture Collection (CCTCC), College of Life Sciences, Wuhan University, Wuhan, Hubei 430072, China.

The potato inbred line "A6-10" was deposited on Apr. 13, 2022, according to the Budapest Treaty in the China Center for Type Culture Collection (CCTCC), College of Life Sciences, Wuhan University, Wuhan, Hubei 430072, China. The deposit has been assigned CCTCC number P202204. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the CCTCC depository, which is a public depository, for a period of at least 30 years, or at least 5 years after the most recent request for a sample of the deposit, or for the effective life of the patent, whichever is longer, and will be replaced if a deposit becomes nonviable during that period.

Potato Inbred Line "E4-63"

A deposit of the potato inbred line "E4-63" is maintained by the Agricultural Genomics Institute at Shenzhen, Chinese Academy of Agricultural Sciences, Shenzhen, Guangdong 518120, China. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the China Center for Type Culture Collection (CCTCC), College of Life Sciences, Wuhan University, Wuhan, Hubei 430072, China.

The potato inbred line "E4-63" was deposited on Apr. 19, 2022, according to the Budapest Treaty in the China Center for Type Culture Collection (CCTCC), College of Life Sciences, Wuhan University, Wuhan, Hubei 430072, China. The deposit has been assigned CCTCC number P202212. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the CCTCC depository, which is a public depository, for a period of at least 30 years, or at least 5 years after the most recent request for a sample of the deposit, or for the effective life of the patent, whichever is longer, and will be replaced if a deposit becomes nonviable during that period.

Potato Inbred Line "E4-64"

A deposit of the potato inbred line "E4-64" is maintained by the Agricultural Genomics Institute at Shenzhen, Chinese Academy of Agricultural Sciences, Shenzhen, Guangdong 518120, China. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the China Center for Type Culture Collection (CCTCC), College of Life Sciences, Wuhan University, Wuhan, Hubei 430072, China.

The potato inbred line "E4-64" was deposited on Aug. 30, 2022 according to the Budapest Treaty in the China Center for Type Culture Collection (CCTCC), College of Life Sciences, Wuhan University, Wuhan, Hubei 430072, China. The deposit has been assigned CCTCC number P202220. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the CCTCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed is:

1. An inbred diploid potato line, wherein the inbred diploid potato line is fertile, has at least 85% of genome homozygosity, and has self-compatibility conferred by (a) a low-expressed S-RNase allele $S_{S11}$ as found in potato clone "A6-10", representative seeds of which having been deposited with CCTCC under accession number P202204, or (b) a S-locus inhibitor (Sli) gene as found in potato clone "E4-63" or "E4-64", representative seeds of which having been deposited with CCTCC under accession number P202212 and P202220, respectively.

2. The inbred diploid potato line of claim 1, wherein the inbred diploid potato line comprises at least one agronomically desired trait selected from the group consisting of strong growth vigor, high yield, improved nutritional value, insect tolerance, nematode resistance, disease resistance, herbicide tolerance, cold tolerance, drought tolerance, wet tolerance, tolerance to dry and wet rot, salinity tolerance, and cold-sweetening resistance.

3. The inbred diploid potato line of claim 1, wherein the inbred diploid potato line produces tubers having a carotenoid content of: (a) at least 40 mg/kg dry-weight and/or (b) a dry matter percentage of at least 20%.

4. A plant, seed, tuber, or plant part of the inbred diploid potato line of claim 1.

5. A method for producing $F_1$ hybrid potato seed, comprising:
   (a) obtaining a first self-compatible diploid potato plant, wherein self-compatibility in the first self-compatible diploid potato plant is conferred by (i) a low-expressed S-RNase allele $S_{S11}$ as found in potato clone "A6-10", representative seeds of which having been deposited with CCTCC under accession number P202204, or (ii) a S-locus inhibitor (Sli) gene as found in potato clone "E4-63" or "E4-64", representative seeds of which having been deposited with CCTCC under accession number P202212 and P202220, respectively and a second self-compatible diploid potato plant;
   (b) selfing the first self-compatible diploid potato plant to obtain a first progeny population and selfing the second self-compatible diploid potato plant to obtain a second progeny population;
   (c) selecting from the first and second progeny populations one or more progeny potato plants having genome homozygosity of at least 60%;
   (d) repeating steps (b) to (c) 2 to 4 times on the selected progeny plant in each of the first and second progeny populations to obtain inbred potato lines having at least 90% of genome homozygosity; and
   (e) generating $F_1$ hybrid potato seed by crossing an inbred line from the first progeny population and an inbred line from the second progeny population.

6. A method for producing $F_1$ hybrid potato seed, comprising:
   (a) obtaining a first self-compatible diploid potato clone, wherein self-compatibility in the first self-compatible diploid potato clone is conferred by (a) a low-expressed S-RNase allele $S_{S11}$ as found in potato clone "A6-10", representative seeds of which having been deposited with CCTCC under accession number P202204, or (b) a S-locus inhibitor (Sli) gene as found in potato clone "E4-63" or "E4-64", representative seeds of which having been deposited with CCTCC under accession number P202212 and P202220, respectively and a second self-compatible diploid potato clone;
   (b) selfing the first self-compatible diploid potato clone to obtain a first progeny population and selfing the second self-compatible diploid potato clone to obtain a second progeny population;
   (c) performing genetic analysis on the first and second progeny populations to identify (i) one or more deleterious mutations selected from the group consisting of yellow leaf 1 (yl1) that leads to leaf yellowing, floral bud abortion 1 (fba1) that leads to abortion of floral buds before flowering, and large-effect deleterious mutation 1 (led1) that negatively impacts the survival of homozygotes; and
   (ii) one or more beneficial alleles selected from the group consisting of an S-RNase S11 ($S_{S11}$) allele for self-compatibility, a Yellow Leaf 1 (YL1) allele for normal leaves, a Floral Bud Abortion 1 (FBA1) allele for fertility, and a Yellow (Y) allele for yellow tuber flesh in the genomes of the progeny populations;
   (d) using genome-assisted selection to select progeny lines having fewer of the deleterious mutations and more of the beneficial alleles in each of the first and second progeny populations;
   (e) repeating steps (b) to (d) 2 to 4 times on the selected progeny lines in each of the first and second progeny populations to obtain inbred potato lines having at least 90% of genome homozygosity; and
   (f) generating $F_1$ hybrid potato seed by crossing an inbred line from the first progeny population and an inbred line from the second progeny population.

7. The method of claim 6, wherein the method further comprises a genetic analysis of genome-wide segregation distortions (SDs) in the progeny populations.

8. The method of claim 6, wherein the genome-assisted selection comprises reducing the number of the deleterious mutations, breaking tight linkage of the deleterious mutations, and/or stacking the beneficial alleles in the genome.

9. A method for producing a hybrid potato seed, the method comprising crossing a first potato plant with a second potato plant and harvesting a hybrid potato seed resulting from the cross, wherein the first potato plant or the second potato plant is derived from the inbred diploid potato line of claim 1.

10. A method for producing a hybrid potato plant, the method comprising producing a seed according to the method of claim 9, and growing the seed into a potato plant.

11. The method of claim 10, the method comprising:
   (a) providing a first potato plant, wherein the first potato plant is a plant of potato line "A6-10", representative seeds of which having been deposited with CCTCC under accession number P202204;

(b) providing a second potato plant, wherein the second potato plant is a plant of potato line "E4-63" or "E4-64", representative seeds of which having been deposited with CCTCC under accession number P202212 and P202220, respectively; and
(c) cross-pollinating the first potato plant and the second potato plant to provide seeds and collecting the seeds to thereby provide a hybrid potato line.

* * * * *